(12) United States Patent
Lemoine et al.

(10) Patent No.: US 8,454,700 B2
(45) Date of Patent: Jun. 4, 2013

(54) INTERBODY VERTEBRAL SPACER

(75) Inventors: Jeremy J. Lemoine, Leander, TX (US);
Charles H. Perrone, Jr., Austin, TX (US); Eric M. Simon, Austin, TX (US); Daniel A. Carlson, St. Louis Park, MN (US); Hugh D. Hestad, Edina, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

(21) Appl. No.: 13/252,247

(22) Filed: Oct. 4, 2011

(65) Prior Publication Data
US 2013/0085573 A1    Apr. 4, 2013

(51) Int. Cl.
*A61F 2/44* (2006.01)
(52) U.S. Cl.
USPC ............. 623/17.16; 623/17.11; 606/249
(58) Field of Classification Search
USPC ............. 606/246–249; 623/17.11–17.16
See application file for complete search history.

(56) References Cited

U.S. PATENT DOCUMENTS

| | | | |
|---|---|---|---|
| 5,397,364 A | 3/1995 | Kozak et al. | |
| 5,800,547 A | 9/1998 | Schafer et al. | |
| 6,045,579 A | 4/2000 | Hochshuler et al. | |
| 6,102,949 A | 8/2000 | Biedermann et al. | |
| 6,102,950 A | 8/2000 | Vaccaro | |
| 6,179,873 B1 | 1/2001 | Zientek | |
| 6,641,614 B1 * | 11/2003 | Wagner et al. | 623/17.15 |
| 6,770,096 B2 | 8/2004 | Bolger et al. | |
| 7,214,243 B2 | 5/2007 | Taylor | |
| 7,717,959 B2 | 5/2010 | William et al. | |
| 7,771,475 B2 | 8/2010 | Michelson | |
| 2003/0060825 A1 | 3/2003 | Alfaro et al. | |
| 2010/0125334 A1 | 5/2010 | Krueger | |

* cited by examiner

*Primary Examiner* — Eduardo C Robert
*Assistant Examiner* — Christina Negrellirodriguez
(74) *Attorney, Agent, or Firm* — Seager, Tufte & Wickhem, LLC

(57) ABSTRACT

An interbody vertebral implant for facilitating fusion of adjacent vertebrae. The implant includes a first end plate, a second end plate, and an intermediate member disposed therebetween. The end plates are configured to allow bone in-growth. The intermediate member may include features to engage the end plates and to prevent over insertion of the intermediate member within the end plates. The implant may include a cavity extending through the composite implant configured to receive bone growth material to facilitate fusion between a first vertebra and a second vertebra.

25 Claims, 22 Drawing Sheets

INTERBODY VERTEBRAL SPACER

TECHNICAL FIELD

The disclosure is directed to composite implants for insertion between adjacent vertebrae. More particularly, the disclosure is directed to interbody vertebral implants for placement between two adjacent vertebrae.

BACKGROUND

Chronic back problems cause pain and disability for a large segment of the population. Frequently, the cause of back pain is traceable to diseased or degenerated disc material between adjacent vertebrae. When the disc material is diseased, the adjacent vertebrae may be inadequately supported, resulting in persistent pain. Surgical techniques have been developed to remove all or part of the diseased disc material and fuse the joint between adjacent vertebral bodies. Stabilization and/or arthrodesis of the intervertebral joint can reduce the pain associated with movement of a diseased intervertebral joint. Spinal fusion may be indicated to provide stabilization of the spinal column for a wide variety of spine disorders including, for example, structural deformity, traumatic instability, degenerative instability, post-resection iatrogenic instability, etc.

Generally, fusion techniques involve partial or complete removal of the diseased disc and implanting a vertebral implant or spacer between the adjacent vertebral bodies to facilitate new bone growth between the vertebrae. The surface area, configuration, orientation, surface texture and deformity characteristics of an interbody spacer or bone graft placed in the disc space can affect the stability of the joint during fusion and thus affect the overall success of a fusion procedure. Accordingly, it may be desirable to provide improved interbody implants for positioning in the disc space between the vertebral bodies of adjacent vertebrae.

In accordance with the present disclosure, implants are disclosed that can be inserted at a fusion site to provide a desired spacing, support, distraction between adjacent vertebral bodies and/or may provide an osteoconductive scaffold for bony ingrowth.

SUMMARY

The disclosure is directed to several alternative designs and methods of assembling interbody vertebral implants, and use thereof.

Accordingly, one illustrative embodiment is an interbody vertebral implant for facilitating fusion of adjacent vertebrae. The interbody vertebral implant includes a posterior side configured to generally align with the posterior side surface of the vertebral body and an anterior side opposite the posterior side. The implant includes a first end plate, a second end plate, and an intermediate member disposed there between. The intermediate member includes a first arm extending along a first lateral side, a second arm extending along a second lateral side, and a central arm disposed between the first arm and the second arm. The first first arm, the second arm, and the central arm are connected along the posterior side by a connecting member.

Another illustrative embodiment is an interbody vertebral implant for facilitating fusion of adjacent vertebrae. The interbody vertebral implant includes a posterior side configured to generally align with the posterior side surface of the vertebral body and an anterior side opposite the posterior side. The implant includes a first end plate, a second end plate, and an intermediate member disposed there between. The intermediate member is configured such that a first side of the intermediate member engages the first end plate and a second side of the intermediate member engages the second end plate. The intermediate member includes a connecting member, a first arm extending from the connecting member, a second arm extending from the connecting member, and a central arm extending from the connecting member. The central arm includes a fork having a first prong and a second prong adjacent to the anterior side.

Another illustrative embodiment is an interbody vertebral implant for facilitating fusion of adjacent vertebrae. The interbody vertebral implant includes a posterior side configured to generally align with the posterior side surface of the vertebral body and an anterior side. The implant includes a first end plate, a second end plate, and an intermediate member disposed there between. The intermediate member is configured such that a first side of the intermediate member engages the first end plate and a second side of the intermediate member engages the second end plate. The second side of the first end plate comprises means for engaging the first side of the intermediate member and the first side of the second end plate includes means for engaging the second side of the intermediate member. The intermediate member includes a connecting member extending from a first lateral side to a second lateral side along the posterior side, a first arm extending from the connecting member towards the anterior side along the first lateral side, a second arm extending from the connecting member towards the anterior side along the second lateral side, and a central arm extending from the connecting member towards the anterior side between the first and second arms. The first and second arms include at least one stop member adjacent the anterior side. The central arm includes a fork having a first prong and a second prong adjacent to the anterior side.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
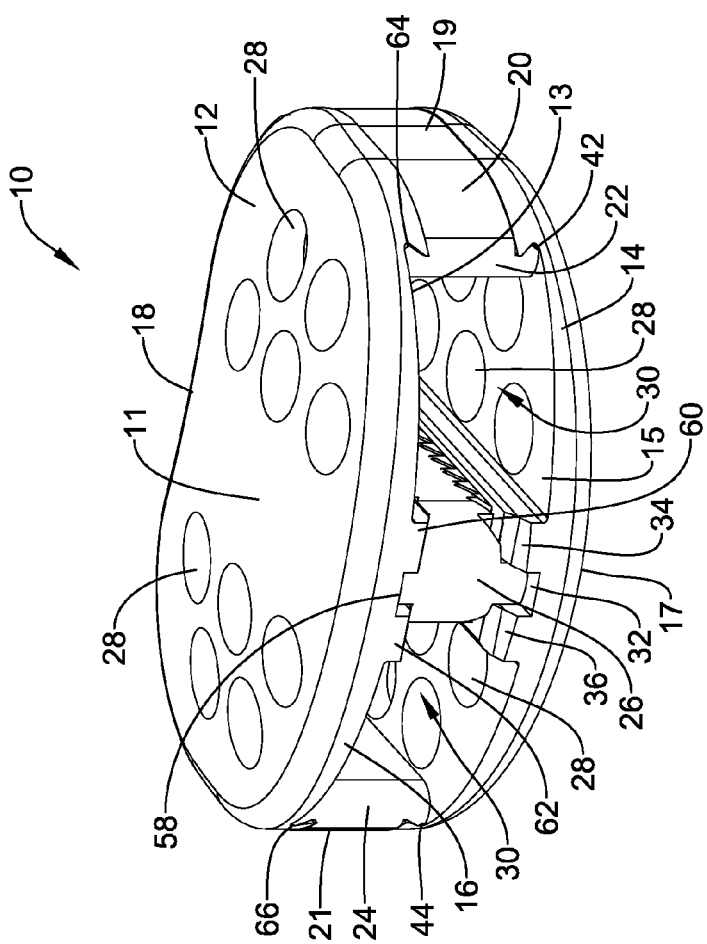
FIG. 1 is a perspective view of an illustrative interbody implant assembly for placement between adjacent vertebrae.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to FIG. 1, there is shown a perspective view of an illustrative interbody spacer assembly 10 for placement between two adjacent vertebrae. The assembly 10 may include an anterior side 16 and a posterior side 18. The assembly 10 may be configured such that when the assembly 10 is inserted between the vertebral bodies of adjacent vertebrae, the posterior side 18 is disposed adjacent to the posterior side of the vertebral bodies of the vertebrae. The spacer assembly 10 may include a first end plate 12, a second end plate 14, and an intermediate member or strut 20 assembled therebetween. The interbody spacer assembly 10 may be formed from a variety of materials, such as, but not limited to: stainless steel, titanium or titanium alloys, porous tantalum, other biocompatible metal alloys, polyether ether ketone (PEEK), or other biocompatible polymers. In some instances, the first end plate 12, second end plate 14, and intermediate member 20 may be formed of the same material. In other embodiments, the end plates 12, 14 and intermediate member 20 may be formed from different materials. For example, in some embodiments, the end plates 12, 14 may be formed of titanium while the intermediate member 20 may be formed of PEEK. It is contemplated that in some embodiments, the end plates 12, 14, the intermediate member 20, and/or other components may each be formed from multiple materials. For example, the end plates 12, 14 and/or the intermediate member 20 may be formed having a titanium core surrounded by PEEK.

The first end plate 12 may include a first side 11 configured to contact and/or engage a first vertebra and a second side 13 configured to engage the intermediate member 20. While not explicitly shown, the first side 11 may include features configured to engage the bone, such as, but not limited to, teeth, serrations, ridges, projections, bumps, grooves, channels or the like. The second end plate 14 may include a first side 15 configured to engage the intermediate member 20 and a second side 17 configured to contact and/or engage a second vertebra adjacent to the first vertebra. The second side 17 may include features such as, but not limited to teeth, serrations, ridges, projections, bumps, grooves, channels or the like to engage the vertebra. In some instances, the first and second end plates 12, 14 may be mirror images when assembled with the intermediate member 20. For example, and as discussed in more detail below, the second side 13 of the first end plate 12 may include similar and/or identical features as the first side 15 of the second end plate 14. Similarly, the first side 11 of the first end plate 12 may include similar and/or identical features as the second side 17 of the second end plate 14. In some instances, the features of the first and second end plates 12, 14 may be identical, and thus interchangeable.

In other instances, each endplate 12, 14 may have a different size, shape, curvature and/or angle. For example, a kit of endplates 12, 14 may be provided during a medical procedure of various sizes, shapes, curvatures and/or angles to accommodate anatomical variations and/or lordosis between vertebrae of a spinal column. For instance, the kit may include several pairs of endplates 12, 14 having vertebral body contacting surfaces of varying angles, such as 0°, 1°, 2°, 3°, 4°, 5°, 6°, and/or 7°, or varying radii of curvature. Thus, in view of the modular nature of the implant assembly 10, a surgeon may select any two of the endplates 12, 14 from the kit to provide a customized implant assembly 10 having a desired configuration for a specific anatomy.

The first and second end plates 12, 14 may be spaced a distance from one another by an intermediate member or strut 20 disposed there between. The intermediate member 20 may provide space between the first and second end plates 12, 14 for the insertion of bone growth material. The intermediate member 20 may be sized so as to provide proper spacing between the adjacent vertebrae. In some instances, the intermediate member 20 may be provided as a kit of multiple intermediate members of varying height and/or lengths such that the spacer assembly 10 may be fitted to the patient. In some embodiments, the intermediate member 20 may have a generally horseshoe shape (see FIG. 2) including one or more arms or extensions 22, 24, 26 extending from a connecting member 90 (see FIG. 2) along the posterior side 18 towards the anterior side 16. In some instances, the intermediate member 20 may include a first arm 22 extending along a first lateral side 19 of the assembly 10 and a second arm 24 extending along a second lateral side 21 of the assembly 10. The intermediate member 20 may further include a central arm 26 disposed between the first and second arms 22, 24. Together the arms 22, 24, 26 may define a plurality of cavities 30 for receiving bone growth material. As will be discussed in more detail with respect to FIGS. 2 and 3 the arms 22, 24, 26 may include features configured to secure the intermediate member 20 to the end plates 12, 14.

The first and second end plates 12, 14 may further include one or more through holes 28 extending from the first side 11 to the second side 13 of the first end plate 12 and from the first side 15 to the second side 17 of the second end plate 14. For clarity, not all of the through holes 28 have been labeled in the drawings. The through holes 28 may allow bone in-growth from the adjacent vertebrae. In some instances, the through holes 28 may be positioned on the end plates 12, 14 such that they are generally aligned with the cavities 30 defined by the intermediate member 20 and the end plates 12, 14. However, it is contemplated that the through holes 28 may be positioned in any manner desired. It is further contemplated that the through holes 28 may take any desired shape such as, but not limited to, circular, square, rectangular, oval, polygonal, etc. While the interbody spacer assembly 10 is illustrated as having a plurality of through holes 28 within each end plate 12, 14, it is contemplated that the assembly 10 may include any number of through holes 28 desired, such as, but not limited to, 1, 2, 3, 4, or more through holes 28. It is further contemplated that in some embodiments one or both end plates 12, 14 may be devoid of through holes 28.

Figure 2:
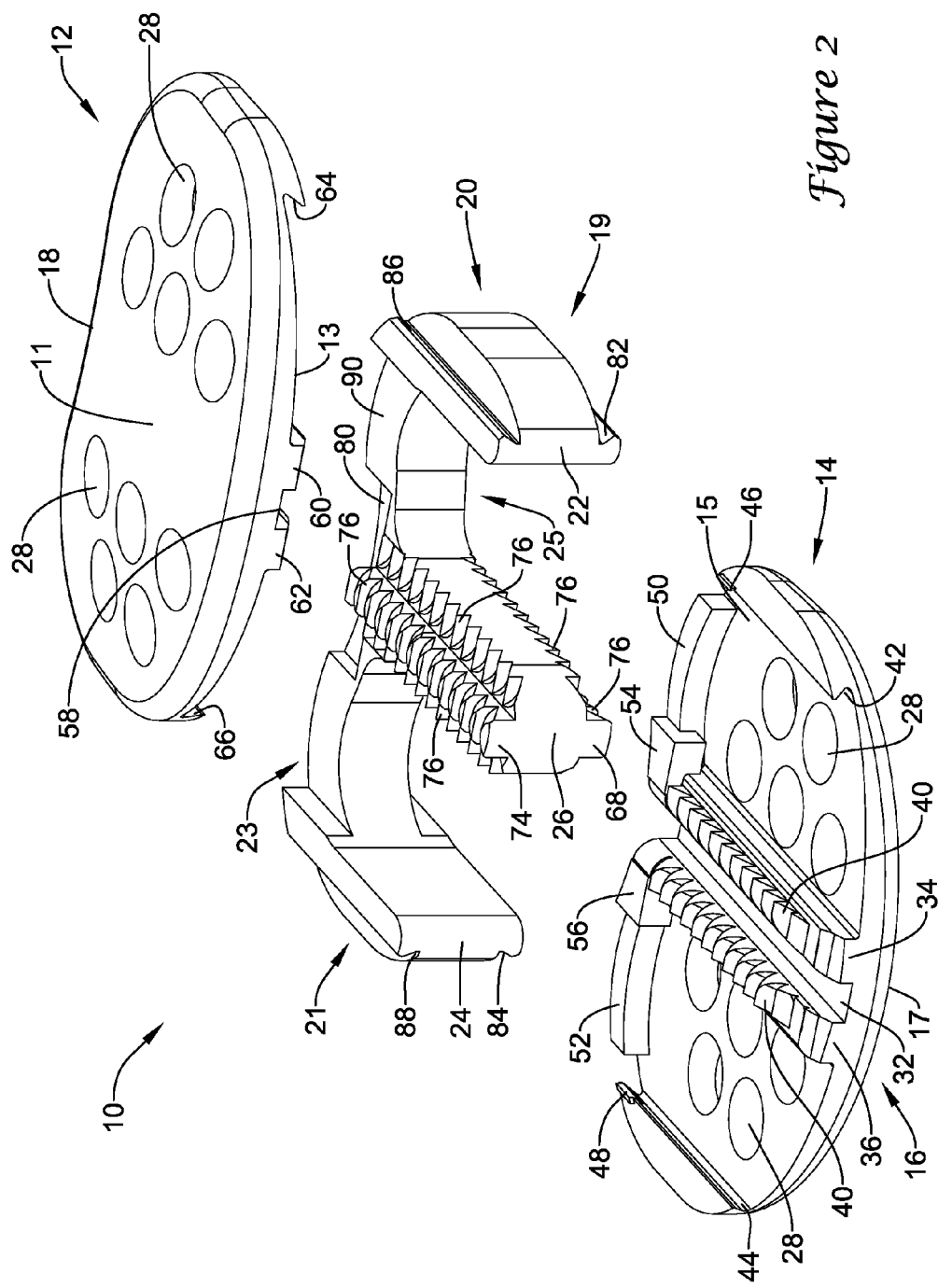
FIG. 2 is an exploded perspective view of the illustrative interbody implant assembly of FIG. 1.

Now referring to FIG. 2, there is shown an exploded perspective view of the illustrative interbody spacer assembly 10 of FIG. 1. The intermediate member 20 may have a generally horseshoe shape formed by a first arm 22, a second arm 24 and a connecting member 90. In some embodiments, the intermediate member 20 may further include a central arm 26 extending from the connecting member 90. In some instances, the intermediate member 20 may include features configured to prevent over insertion of the intermediate member 20 and/or to prevent the intermediate member 20 from disengaging from the end plates 12, 14. The connecting member 90 may include a recessed portion 80 configured to engage a raised portion (not explicitly shown) along the posterior side 18 of the first end plate 12. The second end plate 14 may also include raised portions 54, 56 configured to engage a recessed portion on the second side 25 of the connecting member 90. While not explicitly shown, the recessed portion on the second side 25 of the connecting member 90 may be similar in size and shape to the recessed portion 80 on the first side 23. When the intermediate number 20 is assembled within the end plates 12, 14 the recessed portions 80 may engage the raised portions 54, 56 of the end plates 12, 14 such that the intermediate member 20 may be provided with the stop mechanism to prevent over insertion of the intermediate member 20. It is contemplated that the recesses 80 and raised portions 54, 56 may be sized and shaped to form a generally mating structure. It is further contemplated that the recesses 80 and raised portions 54, 56 may take any shape desired. The second end plate 14 may further include raised portions 50, 52 that in combination with connecting member 90 and similar raised features on the first end plate 12 provide a substantially closed posterior section.

In some instances, the arms 22, 24, 26 may include features configured to engage corresponding features on the end plates 12, 14. For example, the first arm 22 may include a first dovetail groove 86 on a first side 23 of the intermediate member 20 and a second dovetail groove 82 on a second side 25 of the intermediate member 20. The first end plate 12 may include a corresponding dovetail groove 64 configured to mate with the first groove 86 on the first arm 22. The second end plate 14 may include a dovetail groove 42 configured to mate with the second groove 82 on the first arm 22. Similarly, the second arm 24 may include a first dovetail groove 88 on a first side 23 of the intermediate member 20 and a second dovetail groove 84 on a second side 25 of the intermediate member 20. The first end plate 12 may include a corresponding dovetail groove 66 configured to mate with the first groove 88 on the second arm 24. The second end plate 14 may include a dovetail groove 44 configured to mate with the second groove 84 on the second arm 24. When assembled, the mating grooves may align and interlock such that the intermediate member 20 slides between the two end plates 12, 14 and is maintained in a desired orientation. While the grooves have been described as dovetail grooves, it is contemplated the grooves may take any shape desired. It is further contemplated that the grooves may take the shape of some other mating structure. For example, in some instances, the intermediate member 20 may include raised portions configured to engage channels on the end plates 12, 14 or vice versa. In some embodiments, the second end plate 14 may include raised portions 46, 48 disposed adjacent to the dovetail grooves 42, 44 configured to interact with mating elements (not explicitly shown) on the intermediate member 20 and may function as a stop element. While not explicitly shown, the first end plate 12 may include a similar stop mechanism.

The central arm 26 may include features configured to prevent disassembly of the intermediate member 20 once the implant 10 has been assembled, although this is not required. In some instances, the central arm 26 may include two raised portions 74, 68, (e.g. rails) one disposed on either side 23, 25 of the intermediate portion 20. The raised portions 74, 68 may include a plurality of engaging members or teeth 76. The teeth 76 may be of any size and/or shape desired. For example, the teeth 76 may be serrations, ridges, bumps, grooves, etc. While not explicitly shown, in some instances, the teeth 76 may be configured to matingly engage teeth positioned in a central groove 58, 32 (e.g. channel) on the first and second end plates 12, 14. It is further contemplated, that the intermediate member 20 may not include teeth on the raised portion 74, 68. For example, in some instances the raised portions 74, 68 may comprise a smooth surface.

The first side 23 of the central arm 26 may further include a plurality of teeth or serrations 76 disposed on either side of the raised portion 74. Likewise, the second side 25 of the central arm 26 may include a plurality of teeth 76 disposed on either side of the raised portion 68. The teeth 76 may be of any size and/or shape desired. For example, the teeth 76 may be serrations, ridges, bumps, grooves, etc. In some embodiments, the teeth 76, may be configured to engage teeth positioned on raised elements 60, 62, 34, 36 alongside the central groove 58, 32 in the first and second end plates 12, 14. When the intermediate number 20 is assembled with the end plates 12, 14, the orientation of the teeth may allow the intermediate member 20 to be moved in the posterior direction while preventing the intermediate member 20 from being moved in the anterior direction. Thus, the mating engagement of the teeth may prevent the intermediate member 20 from being removed.

Figure 3:
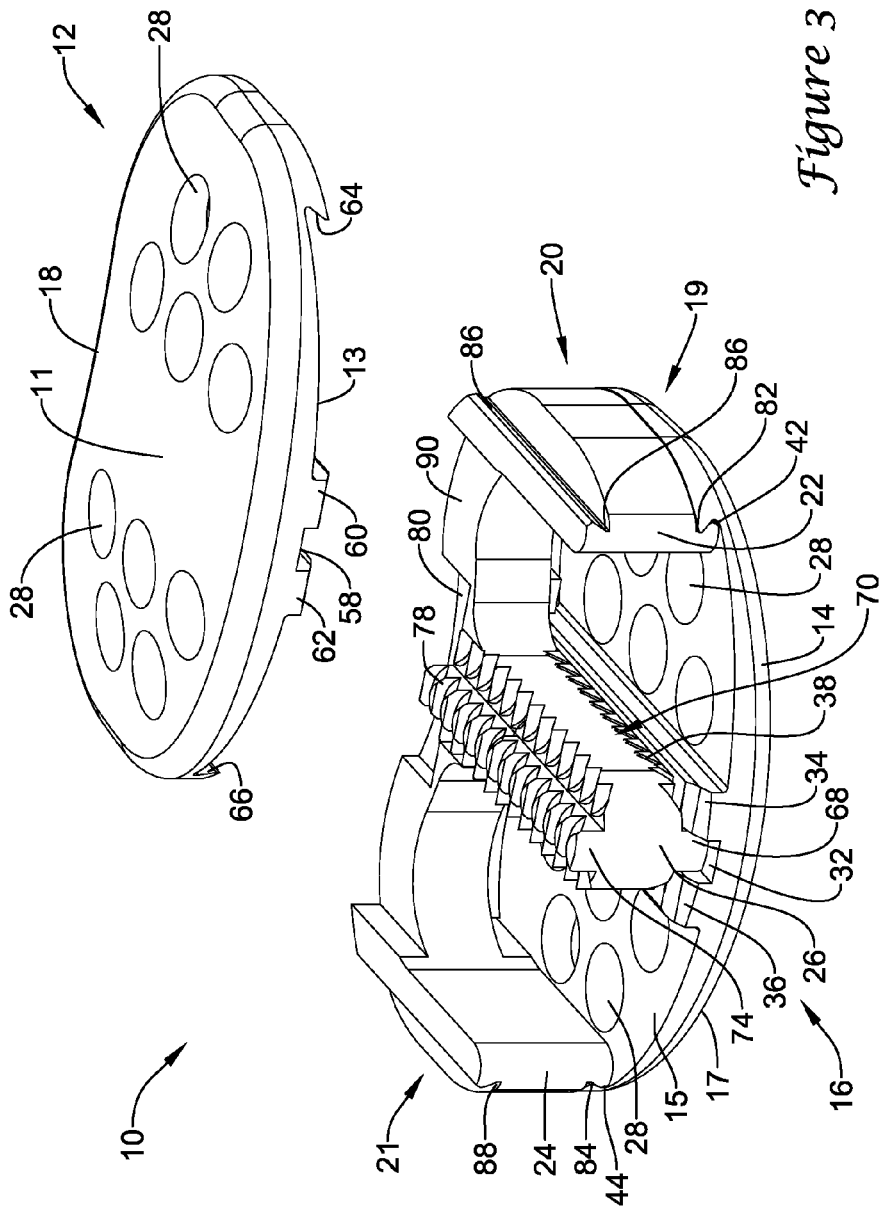
FIG. 3 is an exploded perspective view of the illustrative interbody implant assembly of FIG. 1 partially assembled.

Now referring to FIG. 3, there is shown a partially exploded perspective view of the illustrative interbody spacer assembly 10 of FIG. 1. For illustrative purposes, the intermediate member 20 is shown assembled with the second end plate 14 with the first end plate 12 removed. In some instances, the first and second end plates 12, 14 may be positioned between the vertebral bodies of opposing vertebrae. Once the end plates 12, 14 have been adequately positioned, the intermediate member 20 may be slid between the first and second end plates 12, 14 providing a desired distraction of the vertebrae. For clarity, only the interactions between the second end plate 14 and the intermediate member 20 will be described with respect to FIG. 3. However, it should be understood that the intermediate member 20 and the first end plate 12 may interact in a similar manner as the intermediate member 20 and the second end plate 14.

The intermediate member 20 may be assembled with the second end plate 14 such that the dovetail grooves 82, 84 on the intermediate member 20 engage the dovetail grooves 42, 44 of the second end plate 14 and the raised portion 68 engages the groove 32 of the second end plate 14. The spacer assembly 10 may be assembled by sliding the intermediate member 20 from the anterior side 16 towards the posterior side 18 while aligning the mating grooves. As the intermediate number 20 is installed, the teeth on the central arm 26 may engage the teeth on the second end plate 14. As can be seen in FIG. 3, for example, the teeth 76 adjacent raised portion 68 on the central arm 26 may engage teeth 40 on the raised portion 34 of the second end plate 14. The teeth 40, 70 may be structured such that the intermediate number 20 may be moved in the posterior direction, but are substantially prevented from being moved in the anterior direction. It is contemplated the remaining plurality of teeth on the intermediate number 20 are structured in a similar manner and may engage the plurality of teeth on the first and second end plates 12, 14 in a similar manner. During assembly the intermediate number 20 may be slid in the posterior direction until the recessed portions 80 on the connecting member 90 of the intermediate member 20 engage raised portions (for example, raised portions 54, 56 of the second end plate 14) on the first and second end plates 12, 14. Such engagement may create a stop mechanism to prevent over insertion of the intermediate member 20.

Figure 4:
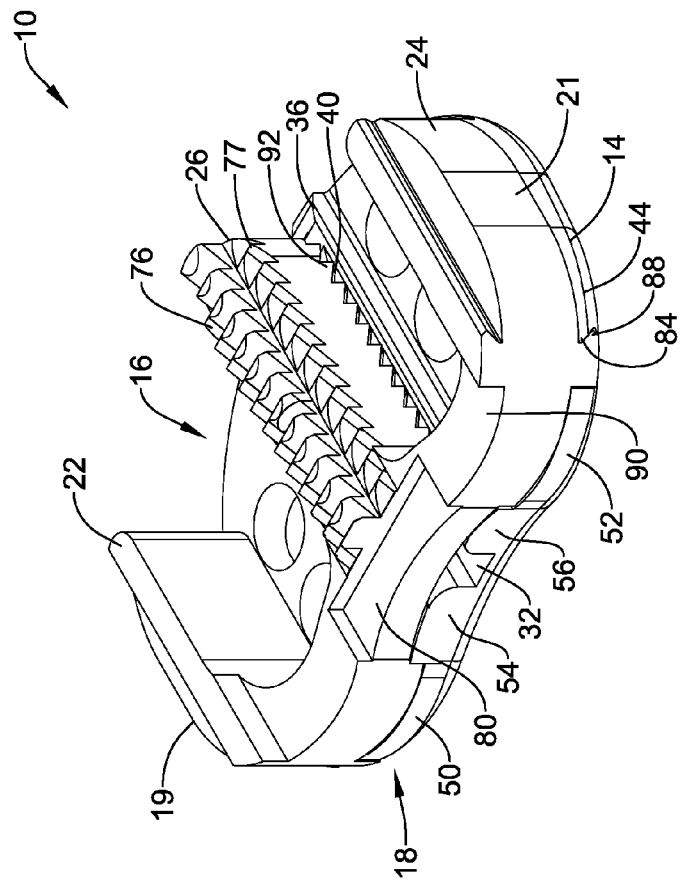
FIG. 4 is a perspective view of the illustrative interbody implant assembly of FIG. 1 partially assembled.

Now referring to FIG. 4, there is shown a partial perspective view of the illustrative interbody spacer assembly 10 of FIG. 1 from the posterior side 18. The first end plate 12 is not illustrated in order to provide a more detailed view of how the intermediate member 20 may engage the second end plate 14. As discussed above, the first and second end plates 12, 14 may include similar, if not identical, features. As such, one of skill in the art will readily appreciate that the features described with respect to the second end plate 14 may be provided on the first end plate 12 and function in a similar manner. When assembled, the posterior side 18 of the assembly 10 may be substantially closed such that bone growth material may be contained within the cavities 30 defined by the first end plate 12, the intermediate member 20, and the second end plate 14. The anterior side 16 of the assembly 10 may remain relatively open allowing for the insertion of bone growth material from the anterior side 16.

Figure 5:
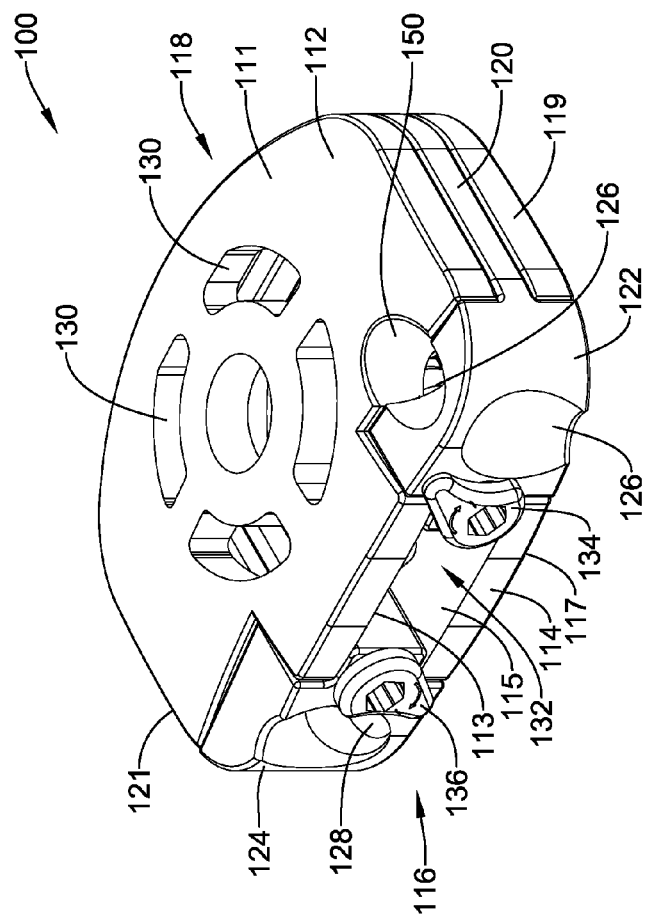
FIG. 5 is a perspective view of an illustrative interbody implant assembly for placement between adjacent vertebrae.

Now referring to FIG. 5, there is shown a perspective view of another illustrative interbody spacer assembly 100 for placement between two adjacent vertebrae. The assembly 100 may include an anterior side 116 and a posterior side 118.

The assembly 100 may be configured such that when the assembly 100 is inserted between the vertebral bodies of adjacent vertebrae, the posterior side 118 is disposed adjacent to the posterior side of the vertebral bodies of the vertebrae. The spacer assembly 100 may include a first end plate 112, a second end plate 114, and an intermediate member or strut 120 insertable therebetween. The interbody spacer assembly 100 may be formed from a variety of materials, such as, but not limited to: stainless steel, titanium or titanium alloys, porous tantalum, other biocompatible metal alloys, polyether ether ketone (PEEK), or other biocompatible polymers. In some instances, the first end plate 112, second end plate 114, and intermediate member 120 may be formed of the same material. In other embodiments, the end plates 112, 114 and/or intermediate member 120 may be formed from different materials. For example, in some embodiments, the end plates 112, 114 may be formed of titanium while the intermediate member 120 may be formed of PEEK. It is contemplated that in some embodiments, the end plates 112, 114, the intermediate member 120, and/or other components may each be formed from multiple materials. For example, the end plates 112, 114 and/or the intermediate member 120 may be formed having a titanium core surrounded by PEEK.

The first end plate 112 may include a first side 111 configured to contact and/or engage a first vertebra and a second side 113 configured to engage the intermediate member 120. While not explicitly shown, the first side 111 may include features configured to engage the bone, such as, but not limited to, teeth, serrations, ridges, projections, bumps, grooves, channels or the like. The second end plate 114 may include a first side 115 configured to engage the intermediate member 120 and a second side 117 configured to contact and/or engage a second vertebra adjacent to the first vertebra. The second side 117 may include features such as, but not limited to teeth, serrations, ridges, projections, bumps, grooves, channels or the like to engage the vertebra. In some instances, the first and second end plates 112, 114 may be mirror images when assembled with the intermediate member 120. For example, and as discussed in more detail below, the second side 113 of the first end plate 112 may include similar and/or identical features as the first side 115 of the second end plate 114. Similarly, the first side 111 of the first end plate 112 may include similar and/or identical features as the second side 117 of the second end plate 114. In some instances, the features of the first and second end plates 112, 114 may be identical, and thus interchangeable.

In other instances, each endplate 112, 114 may have a different size, shape, curvature and/or angle. For example, a kit of endplates 112, 114 may be provided during a medical procedure of various sizes, shapes, curvatures and/or angles to accommodate anatomical variations and/or lordosis between vertebrae of a spinal column. For instance, the kit may include several pairs of endplates 112, 114 having vertebral body contacting surfaces of varying angles, such as 0°, 1°, 2°, 3°, 4°, 5°, 6°, and/or 7°, or varying radii of curvature. Thus, in view of the modular nature of the implant assembly 100, a surgeon may select any two of the endplates 112, 114 from the kit to provide a customized implant assembly 100 having a desired configuration for a specific anatomy.

The first and second end plates 112, 114 may be spaced a distance from one another by an intermediate member or strut 120 disposed there between. The intermediate member 120 may provide space between the first and second end plates 112, 114 for the insertion of bone growth material. The intermediate member 120 may be sized so as to provide proper spacing between the adjacent vertebrae. In some instances, the intermediate member 120 may be provided as a kit including multiple intermediate members 120 of varying height and/or lengths such that the spacer assembly 100 may be fitted to the patient. In some embodiments, the intermediate member 120 may have a generally horseshoe shape (see FIG. 6) including one or more arms or extensions 122, 124 extending from a connecting member 164 (see FIG. 6) along the posterior side 118 towards the anterior side 116. In some instances, the intermediate member 120 may include a first arm 122 extending along a first lateral side 119 of the assembly 100 and a second arm 124 extending along a second lateral side 121 of the assembly 100. The arms 122, 124 and connecting member 164 in combination with the first and second end plates 112, 114 may define a cavity 132 for receiving bone growth material. As will be discussed in more detail with respect to FIGS. 6 and 7 the arms 122, 124 may include features configured to secure the intermediate member 120 to the end plates 112, 114.

The first and second end plates 112, 114 may further include one or more through holes 130 extending from the first side 111 to the second side 113 of the first end plate 112 and from the first side 115 to the second side 117 of the second end plate 114. For clarity, not all of the through holes 130 have been labeled in the drawings. The through holes 130 may allow bone in-growth from the adjacent vertebrae. In some instances, the through holes 130 may be positioned on the end plates 112, 114 such that they are generally aligned with the cavity 132 defined by the intermediate member 120 and the end plates 112, 114. However, it is contemplated that the through holes 130 may be positioned in any manner desired. It is further contemplated that the through holes 130 may take any desired shape such as, but not limited to, circular, square, rectangular, oval, polygonal, etc. While the interbody spacer assembly 100 is illustrated as having a plurality of through holes 130 within each end plate 112, 114, it is contemplated that the assembly 100 may include any number of through holes 130 desired such as, but not limited to, 1, 2, 3, 4, or more through holes 130. It is further contemplated that in some embodiments one or both end plates 112, 114 may be devoid of through holes 130.

In some embodiments, the intermediate member 120 may include a first hole 126 disposed through an enlarged portion 175 of a first arm 122. The first hole 126 may generally align with a recessed portion 150 in the first end plate 112. The first hole 126 in combination with the recessed portion 150 may provide a pathway for receiving a bone screw or other mechanism configured to secure the assembly to a vertebra at an oblique angle. The screw may extend through the hole 126 and into the vertebra adjacent to the first side 111 of the first end plate 112. In some embodiments, the intermediate member 120 may include a second hole 128 disposed through an enlarged portion 177 of a second arm 124. The second hole 128 may generally align with a recessed portion 194 (see FIG. 6) in the second end plate 114. The second hole 128 in combination with the recessed portion 194 may provide a pathway for receiving a bone screw or other mechanism configured to secure the assembly to a vertebra at an oblique angle. The screw may extend through the hole 128 and into the vertebra adjacent to the second side 117 of the second end plate 114.

Figure 6:
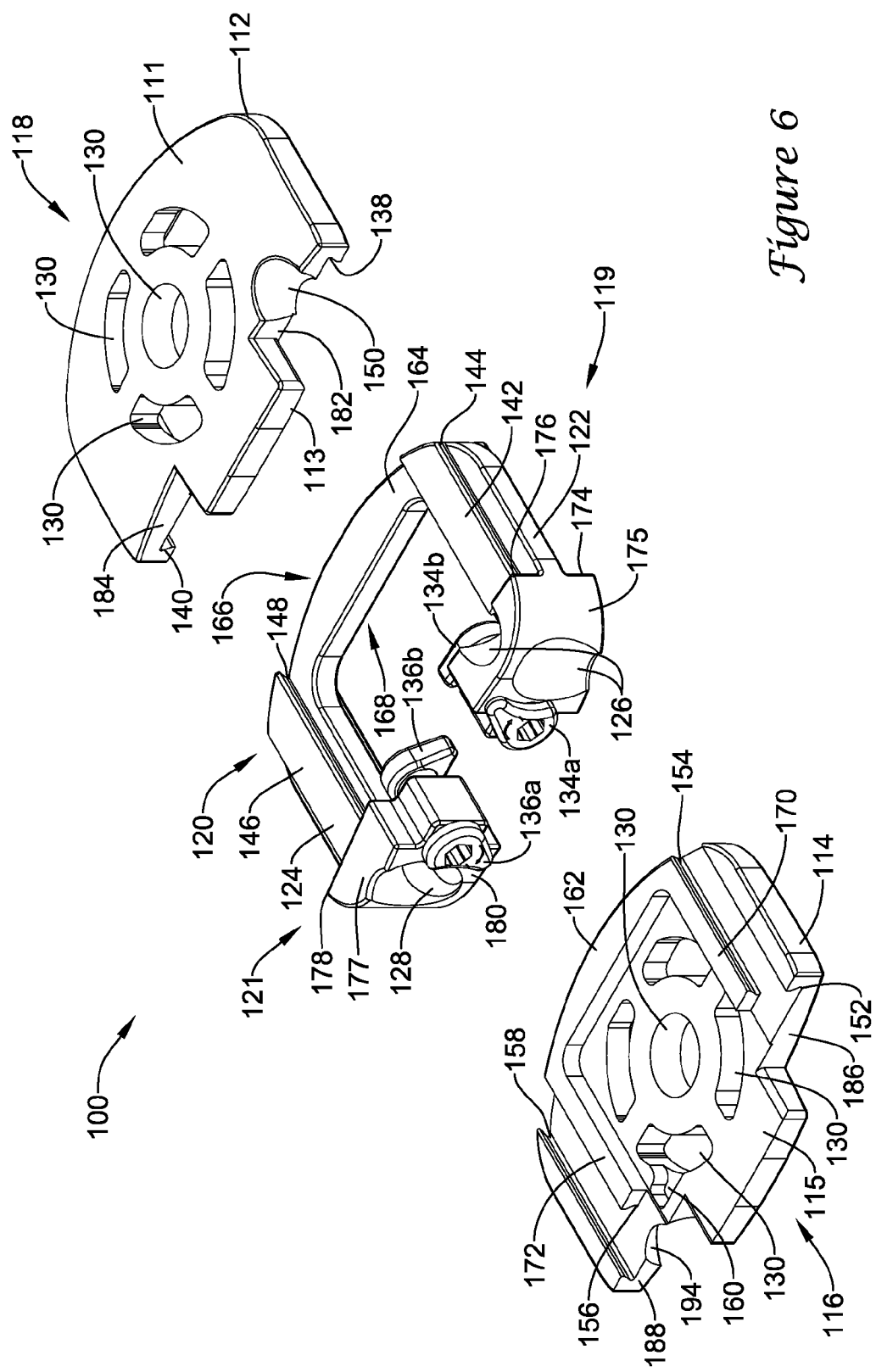
FIG. 6 is an exploded perspective view of the illustrative interbody implant assembly of FIG. 5.

Now referring to FIG. 6, there is shown an exploded perspective view of the illustrative interbody spacer assembly 100 of FIG. 5. The intermediate member 120 may have a generally horseshoe shape formed generally by a first arm 122, a second arm 124 and a connecting member 164. In some instances, the intermediate member 120 may include features configured to prevent over insertion of the intermediate member 120 and/or to prevent the intermediate member 120 from disengaging from the end plates 112, 114. For example, the first arm 122 may include an enlarged region 175 disposed adjacent to the anterior side 116. The enlarged region 175 may include a first portion 176 extending in a first direction and a second portion 174 extending in a second direction. When assembled, the first portion 176 may contact a surface 182 of the first end plate 112 and the second portion 174 may contact a surface 186 of the second end plate 114. The second arm 124 may include an enlarged region 177 disposed adjacent to the anterior side 116. The enlarged region 177 may include a first portion 178 extending in a first direction and a second portion (not explicitly shown) extending in a second direction. When assembled, the first portion 178 may contact a surface 184 of the first end plate 112 and the second portion may contact a surface 188 of the second end plate 114. The enlarged regions 175, 177 in combination with the surfaces 182, 184, 186, 188 of the end plates 112, 114 may prevent the intermediate member 120 from being inserted too far in the posterior direction.

In some instances, the arms 122, 124 may include features configured to engage corresponding features on the end plates 112, 114. For example, first arm 122 may include a raised portion 142 positioned on a first side 166 of the arm 122. The raised portion 142 may include a dovetail groove 144, 145 on either side thereof. The first end plate 112 may include a corresponding pair of dovetail grooves 138, only one of which may be seen in FIG. 6, configured to mate with the grooves 144, 145 on the first raised portion 142. It is contemplated that the dovetail grooves 138 on the first end plate 112 may be similar to the dovetail grooves 152, 154 on the second end plate 114 as described below. While not explicitly shown in FIG. 6, the first arm 122 may include a second raised portion 190 (see FIG. 8) positioned on a second side 168 of the arm 122. The second raised portion 190 may include a dovetail groove 151, 153 on either side thereof. The second end plate 114 may include a corresponding pair of dovetail grooves 152, 154 configured to mate with the grooves 151, 153 on the second raised portion 190. The grooves 152, 154 may be spaced a distance apart from each other generally equal to the distance of the raised portion 190. In some instances, the grooves 152, 154 may face each other to generally define a channel for receiving the raised portion 190 of the first arm 122. While the grooves have been described as dovetail grooves, it is contemplated the grooves may take any shape desired. It is further contemplated that the grooves may take the shape of some other mating structure. For example, in some instances, the intermediate member 120 may include raised portions configured to engage channels on the end plates 112, 114, or vice versa.

The second arm 124 may similarly include a raised portion 146 positioned on a first side 166 of the arm 124. The raised portion 146 may include a dovetail groove 148, 149 on either side thereof. The first end plate 112 may include a corresponding pair of dovetail grooves 140, only one of which may be seen in FIG. 6, configured to mate with the grooves 148, 149 on the first raised portion 146. It is contemplated that the dovetail grooves 140 on the first end plate 112 may be similar to the dovetail grooves 156, 158 on the second end plate 114 as described below. While not explicitly shown in FIG. 6, the second arm 124 may include a second raised portion 192 (see FIG. 8) positioned on a second side 168 of the arm 124. The second raised portion 192 may include a dovetail groove 155, 157 on either side thereof. The second end plate 114 may include a corresponding pair of dovetail grooves 156, 158 configured to mate with the grooves 155, 157 on the second raised portion 192. The grooves 156, 158 may be spaced a distance apart from each other generally equal to the distance of the raised portion 192. In some instances, the grooves 156, 158 may face each other to generally define a channel for receiving the raised portion 192 of the second arm 124.

When assembled, the mating grooves may align and interlock such that the intermediate member 120 slides between the two end plates 112, 114 and is maintained in a desired orientation. While the grooves have been described as dovetail grooves, it is contemplated the grooves may take any shape desired. It is further contemplated that the grooves may take the shape of some other mating structure. For example, in some instances, the intermediate member 120 may include raised portions configured to engage channels on the end plates 112, 114, or vice versa.

The second end plate 114 may include a raised portion have a generally horseshoe shape defined by a first arm 170, a second arm 172, and a connecting member 162. The first and second arms 170, 172 and the connecting member 162 may be approximately the same height as the raised portions 190, 192 such that when the spacer assembly 100 is fully assembled a substantially closed cavity 132 is formed. While not expressly shown, the first end plate 112 may include a similar horseshoe shape raised portion to provide a substantially closed cavity 132 for receiving bone growth material.

Figure 7:
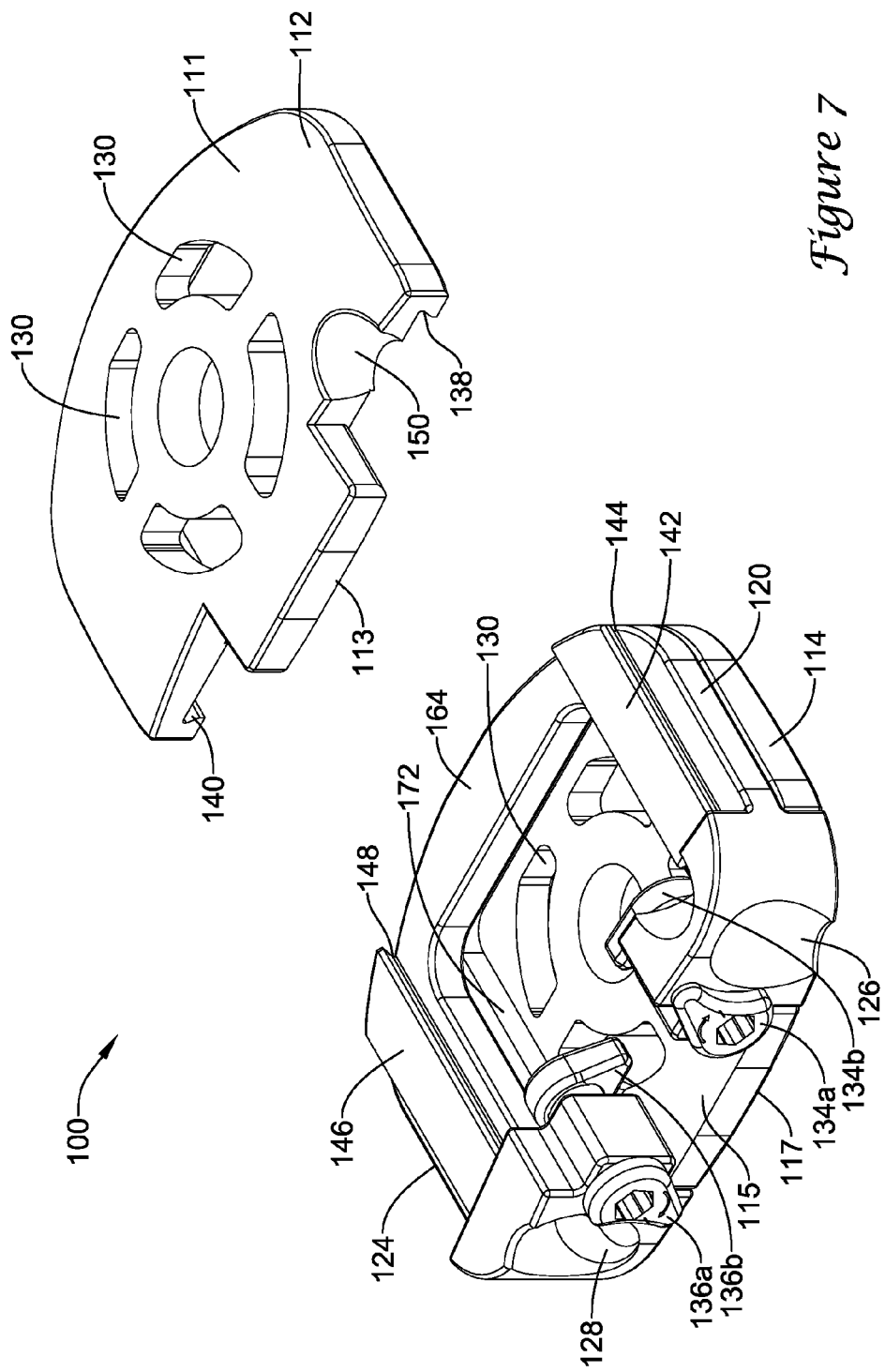
FIG. 7 is an exploded perspective view of the illustrative interbody implant assembly of FIG. 5 partially assembled.

Now referring to FIG. 7, there is shown a partially exploded perspective view of the illustrative interbody spacer assembly 100 of FIG. 5. During assembly of the spacer assembly 100, the intermediate member 120 may be slid between the first and second end plates 112, 114. For clarity, only the interactions between the second end plate 114 and the intermediate member 120 will be described with respect to FIG. 7. However, it should be understood that the intermediate member 120 and the first end plate 112 may interact in a similar manner as the intermediate member 120 and the second end plate 114.

The intermediate member 120 may be assembled with the second end plate 114 such that the dovetail grooves 151, 153, 155, 157 on the intermediate member 120 engage the dovetail grooves 152, 154, 156, 158 of the second end plate 114. The spacer assembly 100 may be assembled by sliding the intermediate member 120 from the anterior side 116 towards the posterior side 118 while aligning the mating grooves. During assembly the intermediate number 120 may be slid in the posterior direction until the second portions 174, 179 of the enlarged regions 175, 177 engage the surface 186, 188 of the second end plate 114. This may create a stop mechanism to prevent over insertion of the intermediate member 120.

In some embodiments, the intermediate member 120 may include a first locking mechanism 134 and a second locking mechanism 136 configured to prevent movement of the intermediate member 120 in the posterior or anterior direction relative to the end plates 112, 114. Once the intermediate member 120 has been installed between the end plates 112, 114, the first and second locking mechanisms 134, 136 may be rotated in a first direction (e.g. the clockwise direction). When the first locking mechanism 134 is rotated a first portion 134a may be disposed over the hole 126. This may help prevent a bone screw, should one be used, from backing out of the bore 126 of the assembly 100. It is further contemplated that upon rotation, a second portion 134b of the locking mechanism 134 may be disposed within a groove (not explicitly shown) in the surface of the second side 113 of the first end plate 112. This may help prevent movement of the intermediate member 120 in the posterior or anterior direction relative to the end plates 112, 114. It is contemplated that the groove may be similar to the groove described with respect to the second locking mechanism 136 and the second end plate 114. When the second locking mechanism 136 is rotated a first portion 136a may be disposed over the hole 128. This may help prevent a bone screw, should one be used, from backing out of the bore 128 of the assembly 100. It is further contemplated that upon rotation, a second portion 136b of the locking mechanism 136 may be disposed within a groove 160 (see FIG. 6) in the surface of the first side 115 of the second end plate 114. This may help prevent movement of the intermediate member 120 in the posterior or anterior direction relative to the end plates 112, 114. While the groove 160 is shown adjacent to a through hole 130, this is not required. The groove 160 may be positioned in any location desired that will allow the second portion 136b of the locking mechanism 136 to engage the groove 160. It is further contemplated that the groove 160 may take any shape or size capable of receiving the locking mechanism. As the actuation of the locking mechanisms 134, 136 may block the holes 126, 128 configured to receive a bone screw or other bone engaging mechanism, actuation of the locking mechanisms 134, 136 may not occur until the spacer assembly 100 has been fully installed between adjacent vertebrae.

Figure 8:
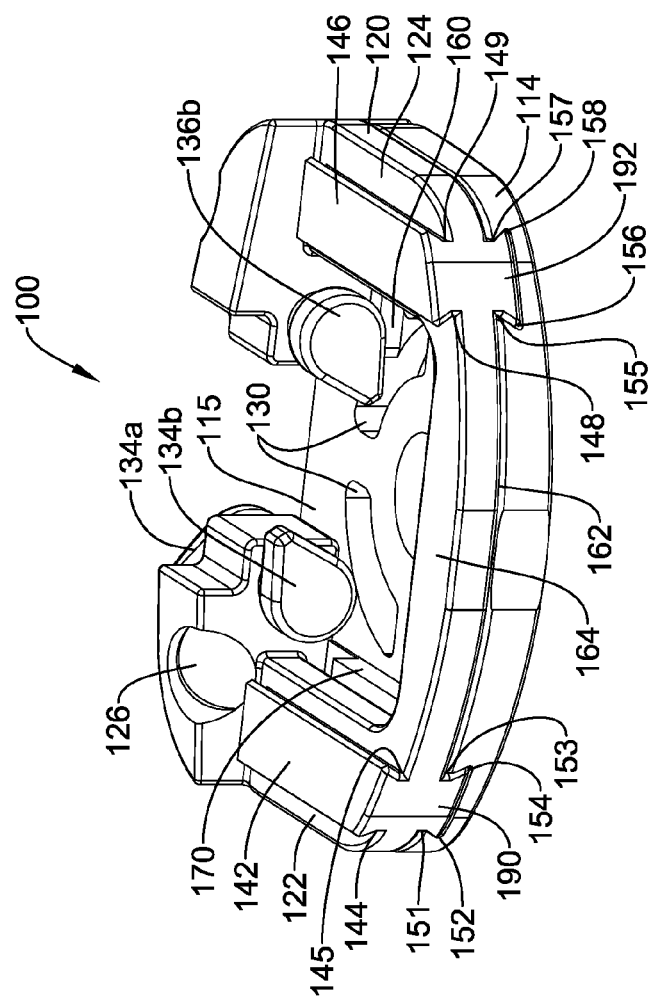
FIG. 8 is a perspective view of the illustrative interbody implant assembly of FIG. 5 partially assembled.

Now referring to FIG. 8, there is shown a partial perspective view of the illustrative interbody spacer assembly 100 of FIG. 5 from the posterior side 118. The first end plate 112 is not illustrated in order to provide a more detailed view of how the intermediate member 120 engages the second end plate 114. As discussed above, the first and second end plates 112, 114 may include similar, if not identical, features. As such, one of skill in the art will readily appreciate that the features described with respect to the second end plate 114 may be provided on the first end plate 112 and function in a similar manner. When assembled, the posterior side 118 of the assembly 100 may be substantially closed such that bone growth material may be contained within the cavitiy 132 defined by the first end plate 112, the intermediate member 120, and the second end plate 114. The anterior side 116 of the assembly 100 may remain relatively open allowing for the insertion of bone growth material from the anterior side 116. As can be seen, the raised portions 190, 192 may be disposed within the channel between the dovetail grooves 152, 154, 156, 158 of the second end plate 114. The grooves 151, 153 of the first arm 122 may be mated with the grooves 152, 154 of the second end plate 114. It can be further seen that the grooves 155, 157 of the second arm 124 may be mated with the grooves 156, 158 of the second end plate 114.

Figure 9:
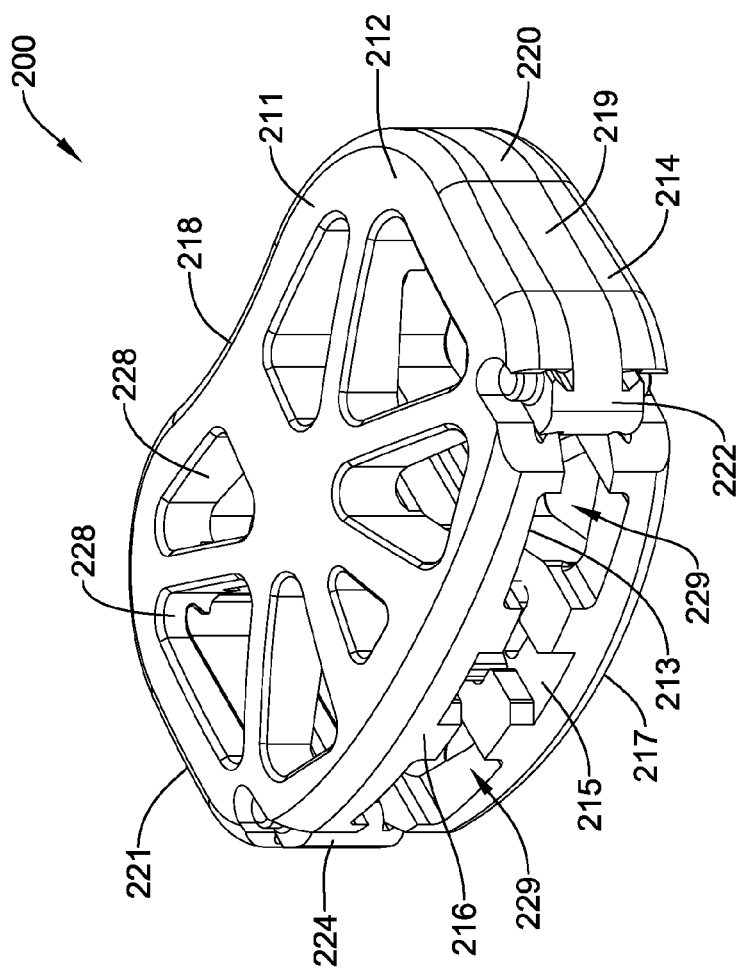
FIG. 9 is a perspective view of an illustrative interbody implant assembly for placement between adjacent vertebrae.

Now referring to FIG. 9, there is shown a perspective view of another illustrative interbody spacer assembly 200 for placement between two adjacent vertebrae. The assembly 200 may include an anterior side 216 and a posterior side 218. The assembly 200 may be configured such that when the assembly 200 is inserted between the vertebral bodies of adjacent vertebrae, the posterior side 218 is disposed adjacent to the posterior side of the vertebral bodies of the vertebrae. The spacer assembly 200 may include a first end plate 212, a second end plate 214, and an intermediate member or strut 220 insertable therebetween. The interbody spacer assembly 200 may be formed from a variety of materials, such as, but not limited to: stainless steel, titanium or titanium alloys, porous tantalum, other biocompatible metal alloys, polyether ether ketone (PEEK), or other biocompatible polymers. In some instances, the first end plate 212, second end plate 214, and/or intermediate member 220 may be formed of the same material. In other embodiments, the end plates 212, 214 and intermediate member 220 may be formed from different materials. For example, in some embodiments, the end plates 212, 214 may be formed of titanium while the intermediate member 220 may be formed of PEEK. It is contemplated that in some embodiments, the end plates 212, 214, the intermediate member 220, and/or other components may each be formed from multiple materials. For example, the end plates 212, 214 and/or the intermediate member 220 may be formed having a titanium core surrounded by PEEK.

The first end plate 212 may include a first side 211 configured to contact and/or engage a first vertebra and a second side 213 configured to engage the intermediate member 220. While not explicitly shown, the first side 211 may include features configured to engage the bone, such as, but not limited to, teeth, serrations, ridges, projections, bumps, grooves, channels or the like. The second end plate 214 may include a first side 215 configured to engage the intermediate member 220 and a second side 217 configured to contact and/or engage a second vertebra adjacent to the first vertebra. The second side 217 may include features such as, but not limited to teeth, serrations, ridges, projections, bumps, grooves, channels or the like to engage the vertebra. In some instances, the first and second end plates 212, 214 may be mirror images when assembled with the intermediate member 220. For example, and as discussed in more detail below, the second side 213 of the first end plate 212 may include similar and/or identical features as the first side 215 of the second end plate 214. Similarly, the first side 211 of the first end plate 212 may include similar and/or identical features as the second side 217 of the second end plate 214. In some instances, the features of the first and second end plates 212, 214 may be identical, and thus interchangeable.

In other instances, each endplate 212, 214 may have a different size, shape, curvature and/or angle. For example, a kit of endplates 212, 214 may be provided during a medical procedure of various sizes, shapes, curvatures and/or angles to accommodate anatomical variations and/or lordosis between vertebrae of a spinal column. For instance, the kit may include several pairs of endplates 212, 214 having vertebral body contacting surfaces of varying angles, such as 0°, 1°, 2°, 3°, 4°, 5°, 6°, and/or 7°, or varying radii of curvature. Thus, in view of the modular nature of the implant assembly 200, a surgeon may select any two of the endplates 212, 214 from the kit to provide a customized implant assembly 200 having a desired configuration for a specific anatomy.

The first and second end plates 212, 214 may be spaced a distance from one another by an intermediate member or strut 220 disposed there between. The intermediate member 220 may provide space between the first and second end plates 212, 214 for the insertion of bone growth material. The intermediate member 220 may be sized so as to provide proper spacing between the adjacent vertebrae. In some instances, the intermediate member 220 may be provided as a kit including multiple intermediate members 220 of varying height and/or lengths such that the spacer assembly 200 may be fitted to the patient. In some embodiments, the intermediate member 220 may have a generally horseshoe shape (see FIG. 10) including one or more arms or extensions 222, 224, 226 extending from a connecting member 223 (see FIG. 10) along the posterior side 218 towards the anterior side 216. In some instances, the intermediate member 220 may include a first arm 222 extending along a first lateral side 219 of the assembly 200 and a second arm 224 extending along a second lateral side 221 of the assembly 200. The intermediate member 220 may further include a central arm 226 disposed between the first and second arms 222, 224. Together the arms 222, 224, 226 may define a plurality of cavities 229 for receiving bone growth material. In some embodiments, the first and second end plates 212, 214 may include recessed portions 225, 227 configured to enlarge the cavities 229. As will be discussed in more detail with respect to FIGS. 10 and 11 the arms 222, 224, 226 may include features configured to secure the intermediate member 220 to the end plates 212, 214.

The first and second end plates 212, 214 may further include one or more through holes 228 extending from the first side 211 to the second side 213 of the first end plate 212 and from the first side 215 to the second side 217 of the second end plate 214. For clarity, not all of the through holes 228 have been labeled in the drawings. The through holes 228 may allow bone in-growth from the adjacent vertebrae. In some instances, the through holes 228 may be positioned on the end plates 212, 214 such that they are generally aligned with the cavities 229 defined by the intermediate member 220 and the end plates 212, 214. However, it is contemplated that the through holes 228 may be positioned in any manner desired. It is further contemplated that the through holes 228 may take any desired shape such as, but not limited to, circular, square, rectangular, oval, polygonal, etc. While the interbody spacer assembly 200 is illustrated as having a plurality of through holes 228 within each end plate 212, 214, it is contemplated that the assembly 200 may include any number of through holes 228 desired such as, but not limited to, 1, 2, 3, 4, or more through holes 228. It is further contemplated that in some embodiments one or both end plates 212, 214 may be devoid of through holes 228.

Figure 10:
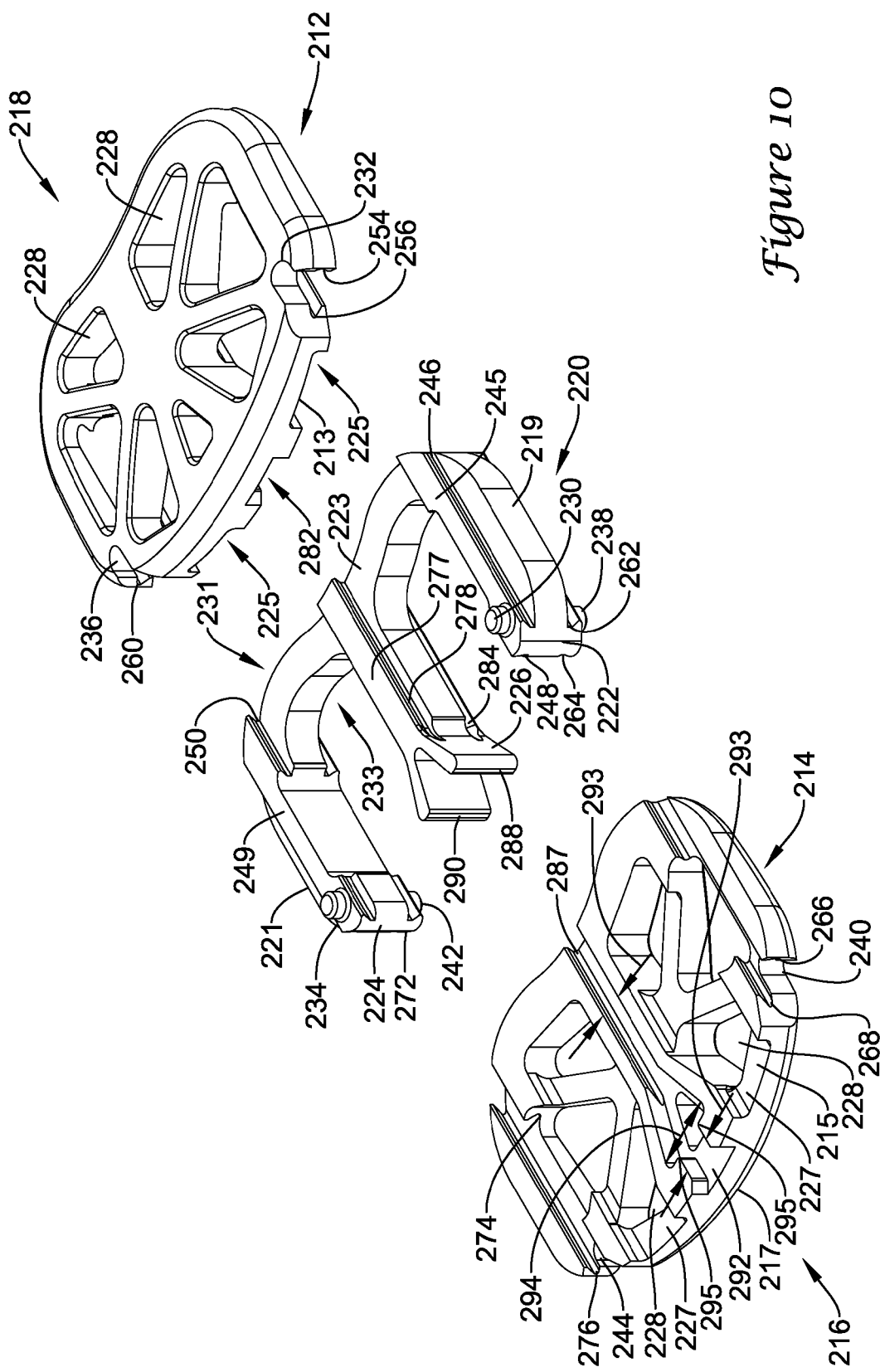
FIG. 10 is an exploded perspective view of the illustrative interbody implant assembly of FIG. 9.

Now referring to FIG. 10, there is shown an exploded perspective view of the illustrative interbody spacer assembly 200 of FIG. 9. The intermediate member 220 may have a generally horseshoe shape formed generally by a first arm 222, a second arm 224 and a connecting member 223. In some instances, the intermediate member 220 may further include a central arm 226 extending from the connecting member 223. In some instances, the intermediate member 220 may include features configured to prevent over insertion of the intermediate member 220 and/or to prevent the intermediate member 220 from disengaging from the end plates 212, 214.

In some embodiments, the arms 222, 224, 226 may include features configured to engage corresponding features on the end plates 212, 214. For example, the first arm 222 may include a first raised portion 245 on a first side 231 of the intermediate member 220. The raised portion 245 may have two dovetail grooves 246, 248 formed on either side thereof. The first end plate 212 may include a corresponding pair of dovetail grooves 254, 256 configured to mate with the grooves 246, 248 on the first side 231 of the first arm 222. The first arm 222 may also include a second raised portion 263 on a second side 233 of the intermediate member 220. The raised portion 263 may have two dovetail grooves 262, 264 formed on either side thereof (see FIG. 12). The second end plate 214 may include a corresponding pair of dovetail grooves 266, 268 configured to mate with the grooves 262, 264 on the second side 233 of the first arm 222.

Similarly, the second arm 224 may include a first raised portion 249 on a first side 231 of the intermediate member 220. The raised portion 249 may have two dovetail grooves 250, 252 formed on either side thereof. The first end plate 212 may include a corresponding pair of dovetail grooves 260 configured to mate with the grooves 250, 252 on the first side 231 of the second arm 224. The second arm 224 may also include a second raised portion 271 on a second side 233 of the intermediate member 220. The raised portion 271 may have two dovetail grooves 270, 272 formed on either side thereof (see FIG. 12). The second end plate 214 may include a corresponding pair of dovetail grooves 274, 276 configured to mate with the grooves 270, 272 on the second side 233 of the second arm 224.

In some embodiments, the central arm 226 may include a first raised portion 277 on a first side 231 of the intermediate member 220. The raised portion 277 may have two dovetail grooves 278, 280 formed on either side thereof. The first end plate 212 may include a corresponding pair of dovetail grooves (not explicitly shown) configured to mate with the grooves 278, 280 on the first side 231 of the central arm 226. The central arm 226 may also include a second raised portion 283 on a second side 233 of the intermediate member 220. The raised portion 283 may have two dovetail grooves 284, 286 formed on either side thereof (see FIG. 12). The second end plate 214 may include a corresponding pair of dovetail grooves 285, 287 configured to mate with the grooves 284, 286 on the second side 233 of the central arm 226.

When assembled, the mating grooves may align and interlock such that the intermediate member 220 slides between the two end plates 212, 214 and is maintained in a desired orientation. While the grooves have been described as dovetail grooves, it is contemplated the grooves may take any shape desired. It is further contemplated that the grooves may take the shape of some other mating structure. For example, in some instances, the intermediate member 220 may include raised portions configured to engage channels on the end plates 212, 214, or vice versa.

In some embodiments, the central arm 26 may further include features configured to prevent disassembly of the intermediate member 220 once the implant 200 has been assembled. For example, in some instances, the central arm 26 may include a 'Y' shaped fork having a first prong 288 and a second prong 290 adjacent to the anterior side 216. During assembly, the raised portions 277, 283 of the central arm 226 may align with channels 282, 292 in the first and second end plates 212, 214. In general, the width of the channels 282, 292 may be approximately equal to the width of the raised portions 277, 283. The prongs 288, 290 of the fork may be spaced a distance apart such that the fork is wider than the width of the raised portions 277, 283. For clarity, only the interactions between the second end plate 214 and the fork prongs 288, 290 will be described with respect to FIG. 11. However, it should be understood that the fork prongs 288, 290 and the first end plate 212 may interact in a similar manner as the fork prongs 288, 290 and the second end plate 214. The channel 292 defined in the second end plate 214 may have a region of enlarged width 294 having a tapered shape similar to the fork prongs 288, 290. The enlarged region 294 may be positioned between two narrower 293 lengths of channel 292 having a width less than the width of the enlarged region 294. As the corresponding mating grooves are aligned and engaged, the intermediate member 220 may be slid in the posterior direction. Once the fork prongs 288, 290 enter the channel 292, the prongs 288, 290 may move (deflect) towards one another allowing the intermediate member 220 to be fully inserted into the second end plate 214. The fork prongs 288, 290 may return to their original orientation once the prongs 288, 290 have entered the enlarged region 294 of the channel 292. Once the prongs 288, 290 have returned to their original orientation, the prongs 288, 290 may prevent anterior movement of the intermediate member 220 by engaging surfaces 295 separating the enlarged region 294 from the narrower region 293 of the channel 292. In some instances, the surfaces may extend generally perpendicular to the channel 292. Thus, when the intermediate member 220 is assembled with the end plates 212, 214, the Y shaped fork prongs 288, 290 may allow the intermediate member 220 to be moved in the posterior direction by compressing while preventing the intermediate member 220 from being moved in the anterior direction.

The intermediate member 220 may further include features configured to prevent the intermediate member 220 from being advanced too far in the posterior direction. In some embodiments, the first arm 222 may include a first stop member or pin 230 extending from the first side 231 and a second pin 238 extending from the second side 233. The first end plate 212 may include a first recessed portion 232 configured to receive the first pin 230. Similarly, the second end plate 214 may include a first recessed portion 240 configured to receive the second pin 238. In some embodiments, the second arm 224 may include a first pin 234 extending from the first side 231 and a second pin 242 extending from the second side 233. The first end plate 212 may include a second recessed portion 236 configured to receive the first pin 234. Similarly, the second end plate 214 may include a second recessed portion 244 configured to receive the second pin 242. While described as pegs, it is contemplated that the stop members 230, 234, 238, 242 may have any shape or size desired configured to engage the recessed portions 232, 236, 240, 244. Likewise, the recessed portions 232, 236, 240, 244 may take any shape or size suitable to receive the stop members 230, 234, 238, 242. When the intermediate member 220 is assembled within the end plates 212, 214 the stop members 230, 234, 238, 242 may abut the recessed portions 232, 236, 240, 244 such that further movement in the posterior direction is prevented.

Figure 11:
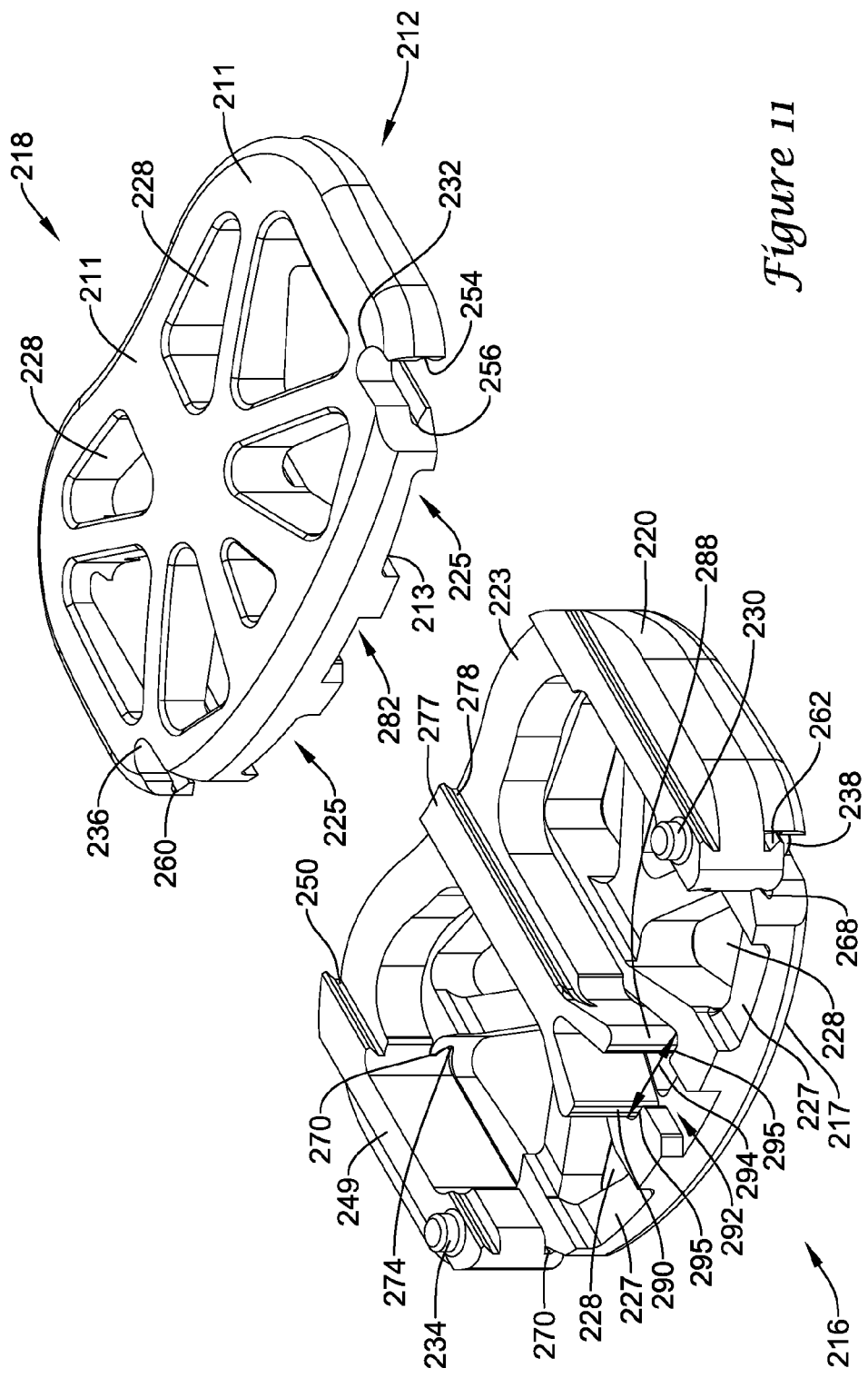
FIG. 11 is an exploded perspective view of the illustrative interbody implant assembly of FIG. 9 partially assembled.

Now referring to FIG. 11, there is shown a partially exploded perspective view of the illustrative interbody spacer assembly 200 of FIG. 9. For illustrative purposes, the intermediate member 220 is shown assembled with the second end plate 214 with the first end plate 212 removed. In some instances, the first and second end plates 212, 214 may be positioned between the vertebral bodies of opposing vertebrae. Once the end plates 212, 214 have been adequately positioned against the vertebral bodies, the intermediate member 220 may be slid between the first and second end plates 212, 214 to effect a desired alignment between the vertebral bodies. For clarity, only the interactions between the second end plate 214 and the intermediate member 220 will be described with respect to FIG. 11. However, it should be understood that the intermediate member 220 and the first end plate 212 may interact in a similar manner as the intermediate member 220 and the second end plate 214.

The intermediate member 220 may be assembled with the second end plate 214 such that the dovetail grooves 262, 264, 284, 286, 270, 272 on the intermediate member 220 engage the dovetail grooves 266, 264, 285, 287, 274, 276 of the second end plate 214 (see also, FIG. 12) and the raised portion 283 engages the groove 292 of the second end plate 214. The spacer assembly 200 may be assembled by sliding the intermediate member 220 from the anterior side 216 towards the posterior side 218 while aligning the mating grooves. As the intermediate member 220 is installed, the prongs 288, 290 may temporarily compress as the central arm 226 is passed through the channel 292. Once in position, the prongs 288, 290 may expand to the original position locking the intermediate member 220 in place. The prongs 288, 290 may abut the surface 295 of the enlarged portion of the channel to prevent, or substantially prevent, subsequent anterior movement of the intermediate member 220. During assembly, the intermediate number 220 may be slid in the posterior direction until the stop members 238, 242 engage the recessed portions 240, 244 on the second end plate 214. This may create a stop mechanism to prevent over insertion of the intermediate member 220.

Figure 12:
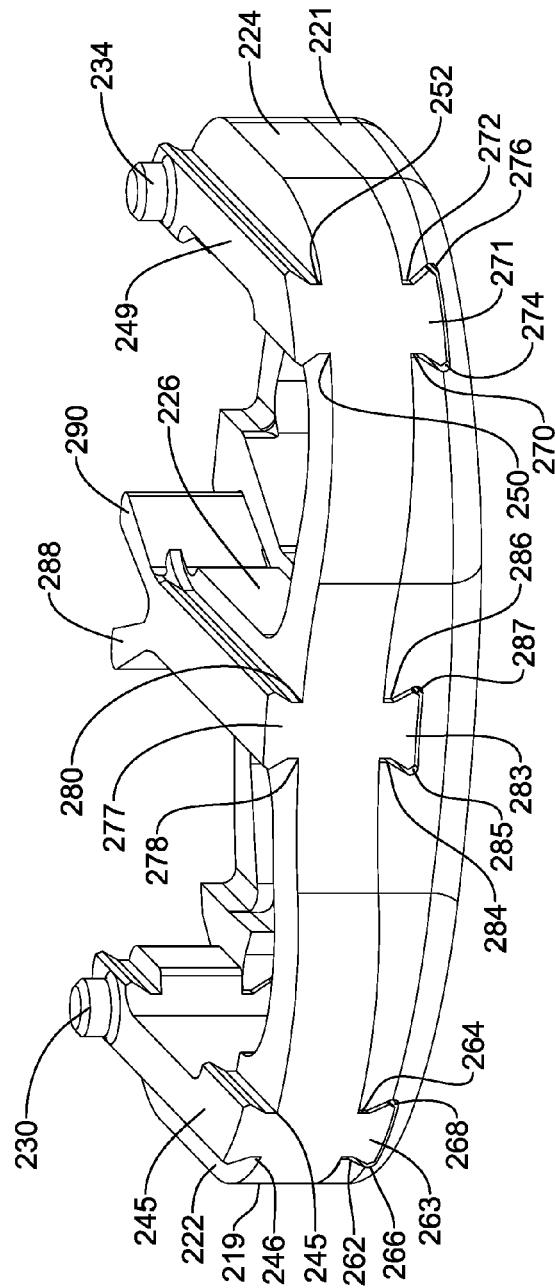
FIG. 12 is a perspective view of the illustrative interbody implant assembly of FIG. 9 partially assembled.

Now referring to FIG. 12, there is shown a partial perspective view of the illustrative interbody spacer assembly 200 of FIG. 9 from the posterior side 218. The first end plate 212 is not illustrated in order to provide a more detailed view of how the intermediate member 220 engages the second end plate 214. As discussed above, the first and second end plates 212, 214 may include similar, if not identical, features. As such, one of skill in the art will readily appreciate that the features described with respect to the second end plate 214 may be provided on the first end plate and function in a similar manner. When assembled, the posterior side 218 of the assembly 200 may be substantially closed such that bone growth material may be contained within the cavities 229 defined by the first end plate 212, the intermediate member 220, and the second end plate 214. The anterior side 216 of the assembly 200 may remain relatively open allowing for the insertion of bone growth material from the anterior side 216.

Figure 13:
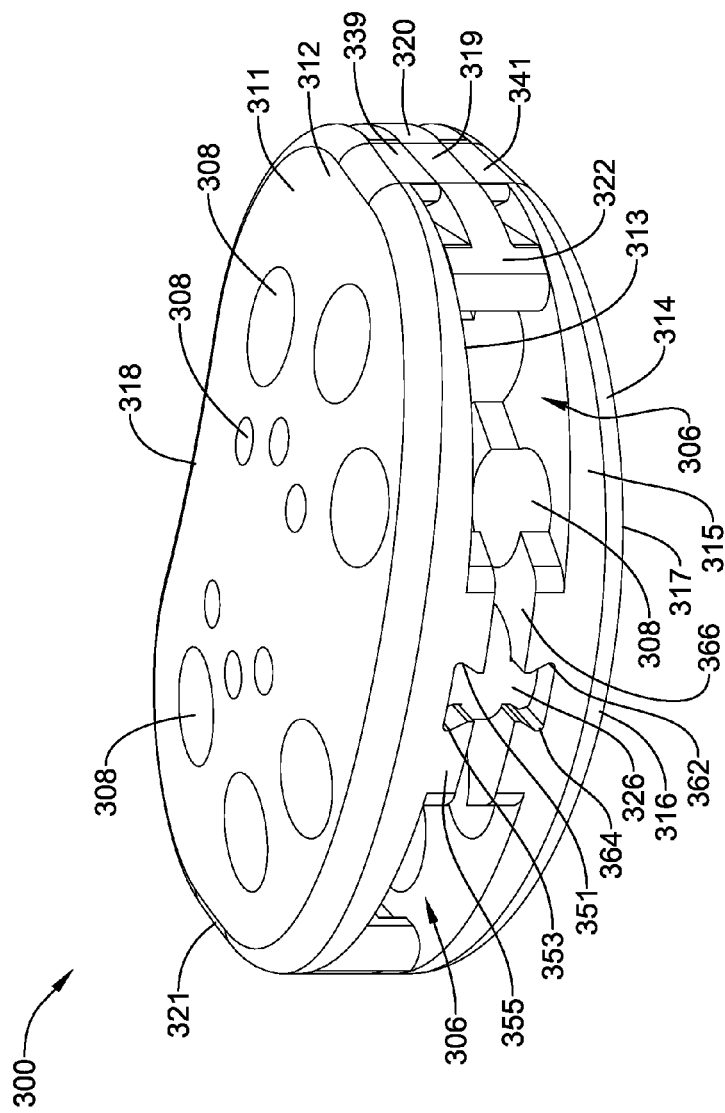
FIG. 13 is a perspective view of an illustrative interbody implant assembly for placement between adjacent vertebrae.

Now referring to FIG. 13, there is shown a perspective view of another illustrative interbody spacer assembly 300 for placement between two adjacent vertebrae. The assembly 300 may include an anterior side 316 and a posterior side 318. The assembly 300 may be configured such that when the assembly 300 is inserted between the vertebral bodies of adjacent vertebrae, the posterior side 318 is disposed adjacent to the posterior side of the vertebral bodies of the vertebrae. The spacer assembly 300 may include a first end plate 312, a second end plate 314, and an intermediate member or strut 320 inserted therebetween. The interbody spacer assembly 300 may be formed from a variety of materials, such as, but not limited to: stainless steel, titanium or titanium alloys, porous tantalum, other biocompatible metal alloys, polyether ether ketone (PEEK), or other biocompatible polymers. In some instances, the first end plate 312, second end plate 314, and intermediate member 320 may be formed of the same material. In other embodiments, the end plates 312, 314 and/or intermediate member 320 may be formed from different materials. For example, in some embodiments, the end plates 312, 314 may be formed of titanium while the intermediate member 320 may be formed of PEEK. It is contemplated that in some embodiments, the end plates 312, 314, the intermediate member 320, and/or other components may each be formed from multiple materials. For example, the end plates 312, 314 and/or the intermediate member 320 may be formed having a titanium core surrounded by PEEK.

The first end plate 312 may include a first side 311 configured to contact and/or engage a first vertebra and a second side 313 configured to engage the intermediate member 320. While not explicitly shown, the first side 311 may include features configured to engage the bone, such as, but not limited to, teeth, serrations, ridges, projections, bumps, grooves, channels or the like. The second end plate 314 may include a first side 315 configured to engage the intermediate member 320 and a second side 317 configured to contact and/or engage a second vertebra adjacent to the first vertebra. The second side 317 may include features such as, but not limited to teeth, serrations, ridges, projections, bumps, grooves, channels or the like to engage the vertebra. In some instances, the first and second end plates 312, 314 may be mirror images when assembled with the intermediate member 320. For example, and as discussed in more detail below, the second side 313 of the first end plate 312 may include similar and/or identical features as the first side 315 of the second end plate 314. Similarly, the first side 311 of the first end plate 312 may include similar and/or identical features as the second side 317 of the second end plate. In some instances, the features of the first and second end plates 312, 314 may be identical, and thus interchangeable.

In other instances, each endplate 312, 314 may have a different size, shape, curvature and/or angle. For example, a kit of endplates 312, 314 may be provided during a medical procedure of various sizes, shapes, curvatures and/or angles to accommodate anatomical variations and/or lordosis between vertebrae of a spinal column. For instance, the kit may include several pairs of endplates 312, 314 having vertebral body contacting surfaces of varying angles, such as 0°, 1°, 2°, 3°, 4°, 5°, 6°, and/or 7°, or varying radii of curvature. Thus, in view of the modular nature of the implant assembly 300, a surgeon may select any two of the endplates 312, 314 from the kit to provide a customized implant assembly 300 having a desired configuration for a specific anatomy.

The first and second end plates 312, 314 may be spaced a distance from one another by an intermediate member or strut 320 disposed there between. The intermediate member 320 may provide space between the first and second end plates 312, 314 for the insertion of bone growth material. The intermediate member 320 may be sized so as to provide proper spacing between the adjacent vertebrae. In some instances, the intermediate member 320 may be provided as a kit including multiple intermediate members 320 of varying height and/or lengths such that the spacer assembly 300 may be fitted to the patient. In some embodiments, the intermediate member 320 may have a generally horseshoe shape (see FIG. 14) including one or more arms or extensions 322, 324, 326 extending from a connecting member 328 (see FIG. 14) along the posterior side 318 towards the anterior side 316. In some instances, the intermediate member 320 may include a first arm 322 extending along a first lateral side 319 of the assembly 300 and a second arm 324 extending along a second lateral side 321 of the assembly 300. The intermediate member 320 may further include a central arm 326 disposed between the first and second arms 322, 324. Together the arms 322, 324, 326 may define a plurality of cavities 306 for receiving bone growth material. As will be discussed in more detail with respect to FIGS. 14 and 15 the arms 322, 324, 326 may include features configured to secure the intermediate member 320 to the end plates 312, 314.

The first and second end plates 312, 314 may further include one or more through holes 308 extending from the first side 311 to the second side 313 of the first end plate 312 and from the first side 315 to the second side 317 of the second end plate 314. For clarity, not all of the through holes 308 have been labeled in the drawings. The through holes 308 may allow bone in-growth from the adjacent vertebrae. In some instances, the through holes 308 may be positioned on the end plates 312, 314 such that they are generally aligned with the cavities 306 defined by the intermediate member 320 and the end plates 312, 314. However, it is contemplated that the through holes 308 may be positioned in any manner desired. It is further contemplated that the through holes 308 may take any desired shape such as, but not limited to, circular, square, rectangular, oval, polygonal, etc. While the interbody spacer assembly 300 is illustrated as having a plurality of through holes 308 within each end plate 312, 314, it is contemplated that the assembly 300 may include any number of through holes 308 desired such as, but not limited to 1, 2, 3, 4, or more through holes 308. It is further contemplated that in some embodiments one or both end plates 312, 314 may be devoid of through holes 308.

Figure 14:
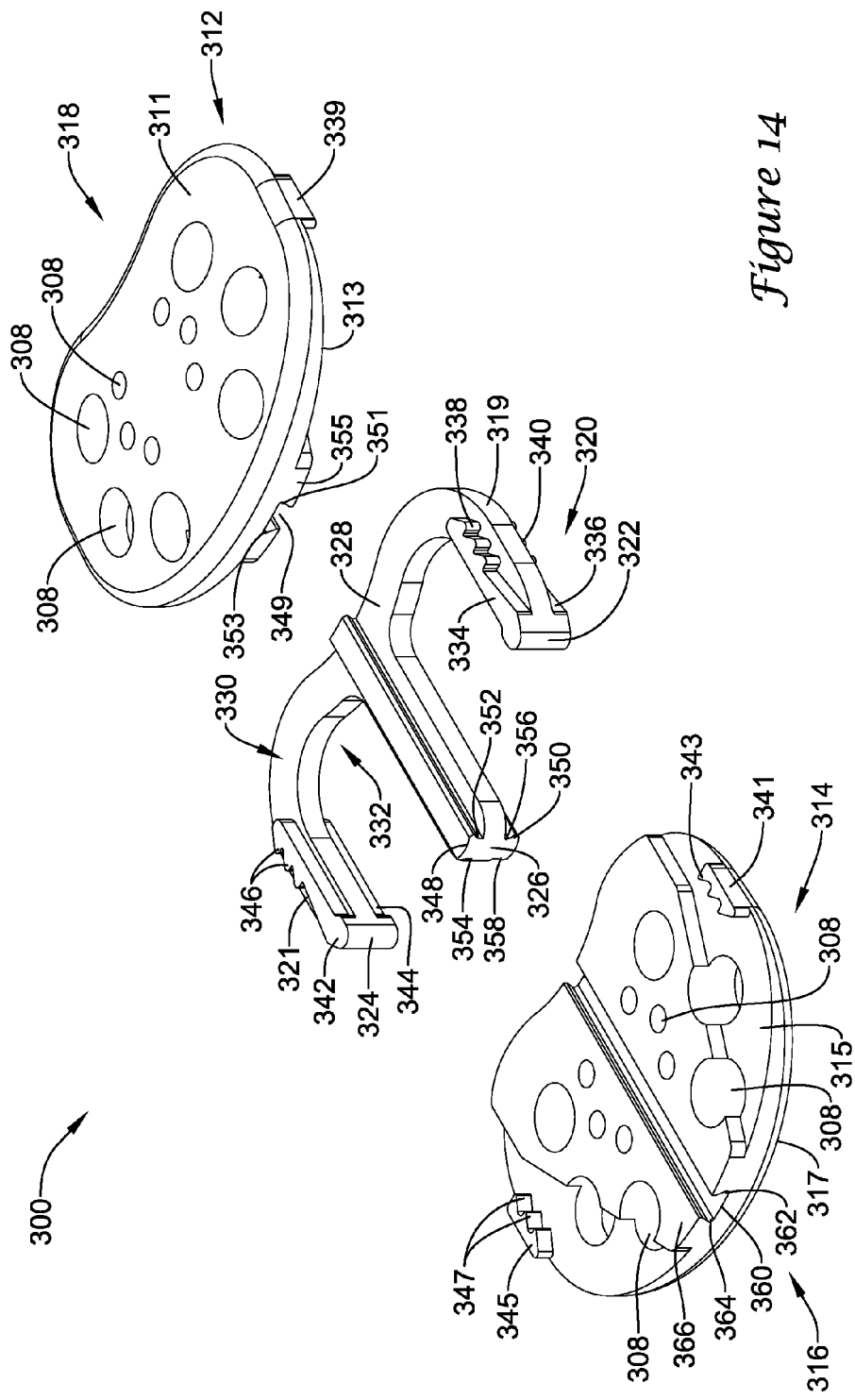
FIG. 14 is an exploded perspective view of the illustrative interbody implant assembly of FIG. 13.

Now referring to FIG. 14, there is shown an exploded perspective view of the illustrative interbody spacer assembly 300 of FIG. 13. The intermediate member 320 may have a generally horseshoe shape formed generally by a first arm 322, a second arm 324 and a connecting member 328. In some instances, the intermediate member 320 may further include a central arm 326 extending from the connecting member 328. In some instances, the intermediate member 320 may include features configured to prevent over insertion of the intermediate member 320 and to prevent the intermediate member 320 from disengaging from the end plates 312, 314.

In some embodiments, the arms 322, 324, 326 may include features configured to engage corresponding features on the end plates 312, 314. For example, the first arm 322 may include a first flexing member 334 disposed on a first side 330 thereof. The flexing member 334 may be configured to flex towards the central arm 326 during insertion of the intermediate member 320 into the end plates 312, 314. The flexing member 334 may include a plurality of engaging members or teeth 338 configured to engage a protruding member 339 of the first end plate 312 including similar mating features such as a plurality of teeth. The first arm 322 may include a second flexing member 336 disposed on a second side 332 thereof. The flexing member 336 may be configured to flex towards the central arm 326 during insertion of the intermediate member 320 into the end plates 312, 314. The flexing member 336 may include a plurality of teeth 340 configured to engage a protruding member 341 of the second end plate 314 including similar mating features such as a plurality of teeth 343. Similarly, the second arm 324 may include a first flexing member 342 disposed on a first side 330 thereof. The flexing member 342 may be configured to flex towards the central arm 326 during insertion of the intermediate member 320 into the end plates 312, 314. The flexing member 342 may include a plurality of teeth 346 configured to engage a protruding member (not explicitly shown) of the first end plate 312 including similar mating features such as a plurality of teeth. The second arm 324 may also include a second flexing member 344 disposed on a second side 332 thereof. The flexing member 344 may be configured to flex towards the central arm 326 during insertion of the intermediate member 320 into the end plates 312, 314. The flexing member 344 may include a plurality of teeth configured to engage a protruding member 345 of the second end plate 314 including similar mating features such as a plurality of teeth 347. The teeth 338, 343, 346, 347 may be of any size and/or shape desired. For example, the teeth 338, 343, 346, 347 may be serrations, ridges, bumps, grooves, or other mating structure.

As mentioned above, the flexing members 334, 336, 342, 344 may be configured to flex inwards towards the central arm 326. This may allow the flexing members 334, 336, 342, 344 to be slightly deformed in order to allow the intermediate member 320 to be moved in the posterior direction and into engagement with the protruding members 339, 341, 345 on the first and second end plates. When the flexing members 334, 336, 342, 344 engage the protruding members 339, 341, 345 the respective teeth may interact such that the intermediate member 320 may not be subsequently moved in the anterior direction. Further, the engagement of the flexing members 334, 336, 342, 344 and the protruding members 339, 341, 345 may create a stop mechanism such that the intermediate member 320 may not be over-inserted in the posterior direction.

In some embodiments, the central arm 326 may include a first raised portion 348 (e.g. rail) on a first side 330 of the intermediate member 320. The raised portion 348 may have two dovetail grooves 352, 354 formed on either side thereof. The first end plate 312 may include a groove 349 defined in a raised portion 355. The groove 349 may include a dovetail groove 351, 353 on either side thereof. The dovetail grooves 351, 353 may be configured to mate with the grooves 352, 354 on the first side 330 of the central arm 326. The central arm 326 may further include a second raised portion 350 on a second side 332 of the intermediate member 320. The raised portion 350 may have two dovetail grooves 356, 358 formed on either side thereof (see FIG. 16). The second end plate 314 may include a groove 360 defined in a raised portion 366. The groove 360 may include a dovetail groove 362, 364 on either side thereof. The dovetail grooves 362, 364 may be configured to mate with the grooves 356, 358 on the second side 332 of the central arm 326.

When assembled, the mating grooves may align and interlock such that the intermediate member 320 slides between the two end plates 312, 314 and is maintained in a desired orientation. While the grooves have been described as dovetail grooves, it is contemplated the grooves may take any shape desired. It is further contemplated that the grooves may take the shape of some other mating structure. For example, in some instances, the intermediate member 320 may include raised portions configured to engage channels on the end plates 312, 314, or vice versa.

Figure 15:
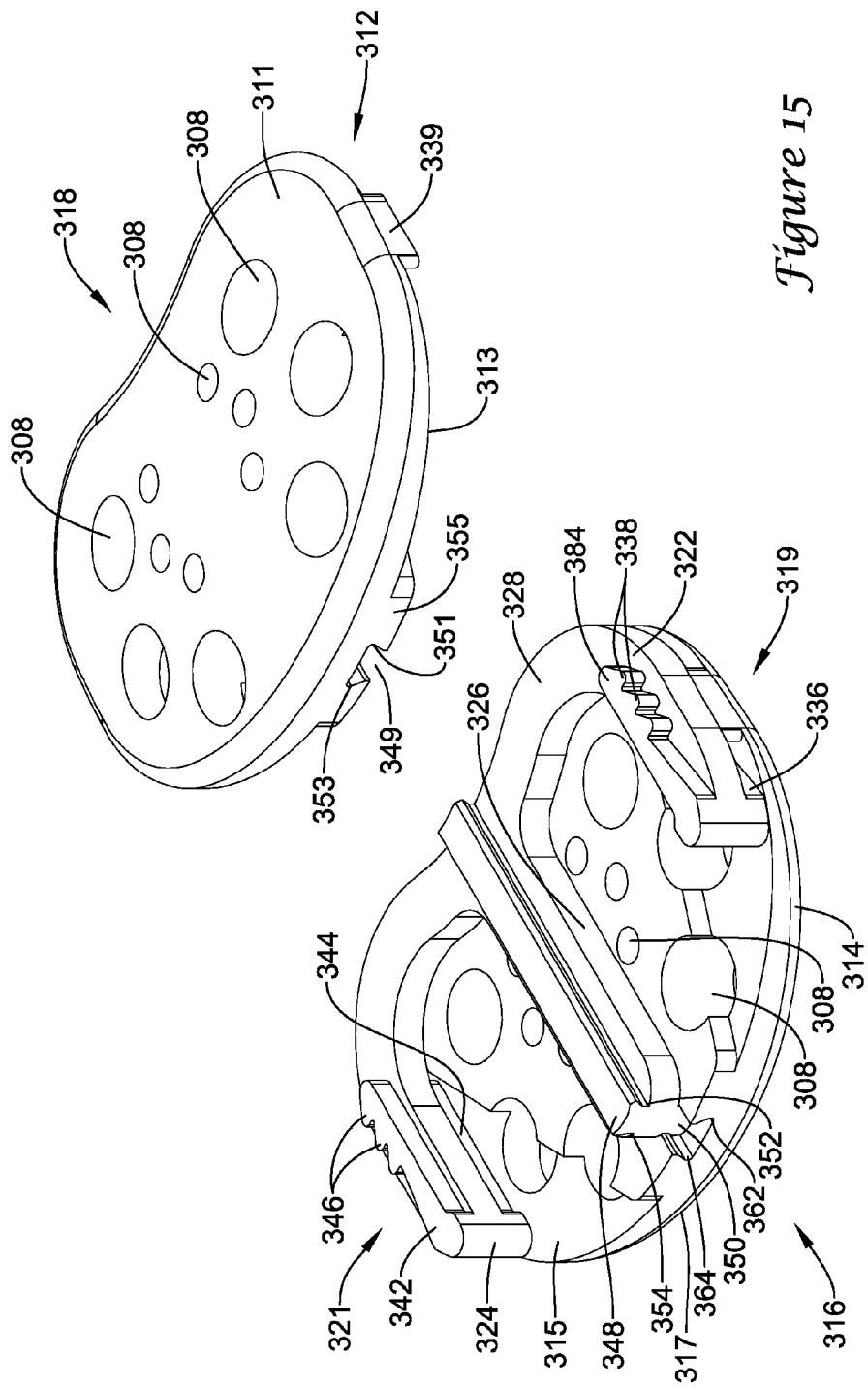
FIG. 15 is an exploded perspective view of the illustrative interbody implant assembly of FIG. 13 partially assembled.

Now referring to FIG. 15, there is shown a partially exploded perspective view of the illustrative interbody spacer assembly 300 of FIG. 13. For illustrative purposes, the intermediate member 320 is shown assembled with the second end plate 314 with the first end plate 312 removed. In some instances, the first and second end plates 312, 314 may be positioned between the vertebral bodies of opposing vertebrae. Once the end plates 312, 314 have been adequately positioned, the intermediate member 320 may be slid between the first and second end plates 312, 314. For clarity, only the interactions between the second end plate 314 and the intermediate member 320 will be described with respect to FIG. 15. However, it should be understood that the intermediate member 320 and the first end plate 312 may interact in a similar manner as the intermediate member 320 and the second end plate 314.

The intermediate member 320 may be assembled with the second end plate 314 such that the dovetail grooves 356, 358 on the intermediate member 320 engage the dovetail grooves 362, 364 of the second end plate 314. The spacer assembly 300 may be assembled by sliding the intermediate member 320 from the anterior side 316 towards the posterior side 318 while aligning the mating grooves. As the intermediate member 320 is installed, the flexing members 336, 344 may bend slightly towards the central arm 326 to allow the teeth 340 of the flexing members 336, 344 to engage the teeth 343, 347 on the protrusions 341, 345 of the second end plate 314. The teeth 340, 343, 347 may be structured such that the intermediate number 320 may be moved in the posterior direction but is substantially prevented from being moved back in the anterior direction. It is contemplated the remaining plurality of teeth on the intermediate number 320 are structured in a similar manner and may engage the plurality of teeth on the first and second end plates 312, 314 in a similar manner. The flexing members 336, 344 and protrusions 341, 345 may also create a stop mechanism to prevent over insertion of the intermediate member 320.

Figure 16:
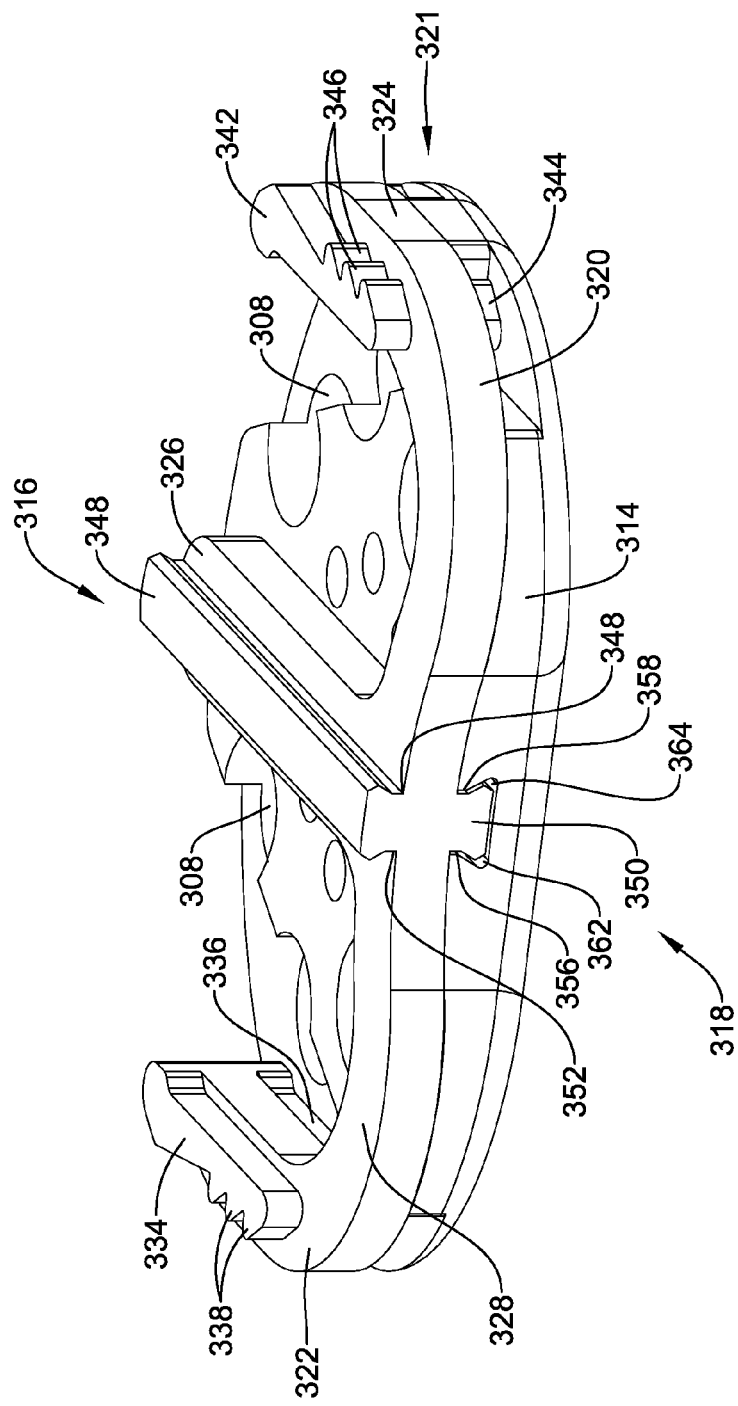
FIG. 16 is a perspective view of the illustrative interbody implant assembly of FIG. 13 partially assembled.

Now referring to FIG. 16, there is shown a partial perspective view of the illustrative interbody spacer assembly 300 of FIG. 13 from the posterior side 318. The first end plate 312 is not illustrated in order to provide a more detailed view of how the intermediate member 320 engages the second end plate 314. As discussed above, the first and second end plates 312, 314 may include similar, if not identical, features. As such, one of skill in the art will readily appreciate that the features described with respect to the second end plate 314 may be provided on the first end plate 312 and function in a similar manner. When assembled, the posterior side 318 of the assembly 300 may be substantially closed such that bone growth material may be contained within the cavities 306 defined by the first end plate 312, the intermediate member 320, and the second end plate 314. The anterior side 316 of the assembly 300 may remain relatively open allowing for the insertion of bone growth material from the anterior side 316.

Figure 17:
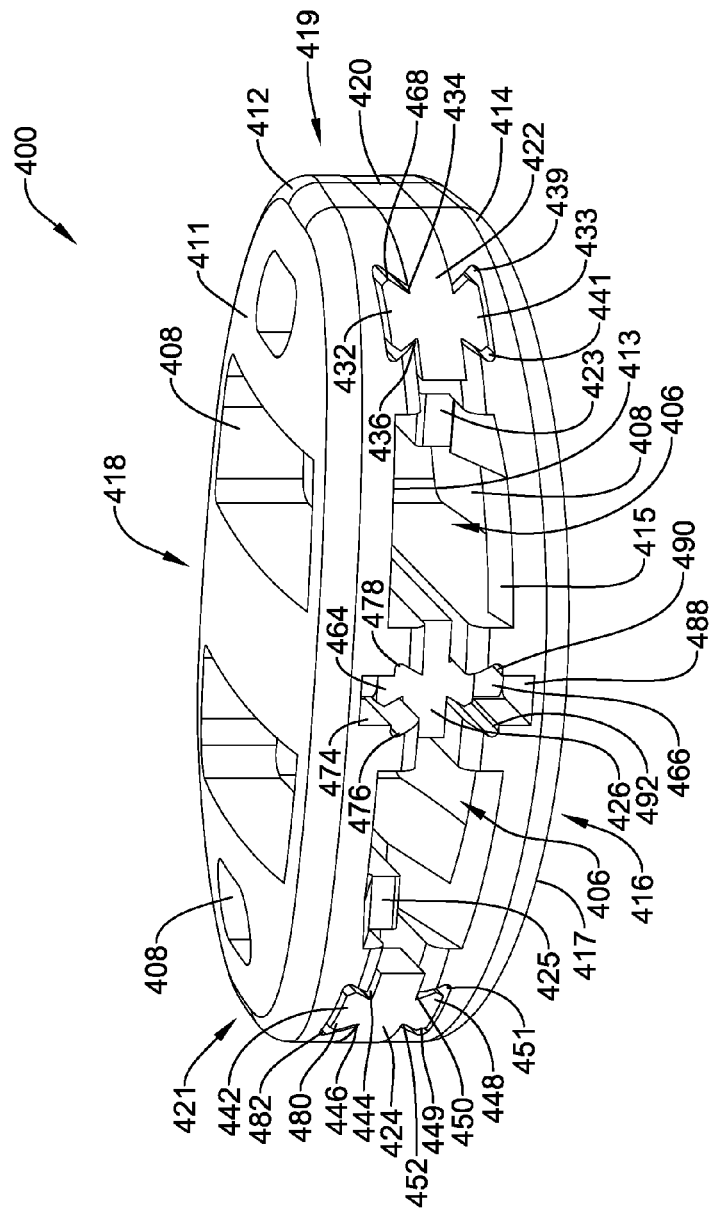
FIG. 17 is a perspective view of an illustrative interbody implant assembly for placement between adjacent vertebrae.

Now referring to FIG. 17, there is shown a perspective view of another illustrative interbody spacer assembly 400 for placement between two adjacent vertebrae. The assembly 400 may include an anterior side 416 and a posterior side 418. The assembly 400 may be configured such that when the assembly 400 is inserted between the vertebral bodies of adjacent vertebrae, the posterior side 418 is disposed adjacent to the posterior side of the vertebral bodies of the vertebrae. The spacer assembly 400 may include a first end plate 412, a second end plate 414, and an intermediate member or strut 420 inserted therebetween. The interbody spacer assembly 400 may be formed from a variety of materials, such as, but not limited to: stainless steel, titanium or titanium alloys, porous tantalum, other biocompatible metal alloys, polyether ether ketone (PEEK), or other biocompatible polymers. In some instances, the first end plate 412, second end plate 414, and intermediate member 420 may be formed of the same material. In other embodiments, the end plates 412, 414 and intermediate member 420 may be formed from different materials. For example, in some embodiments, the end plates 412, 414 may be formed of titanium while the intermediate member 420 may be formed of PEEK. It is contemplated that in some embodiments, the end plates 412, 414, the intermediate member 420, and/or other components may each be formed from multiple materials. For example, the end plates 412, 414 and/or the intermediate member 420 may be formed having a titanium core surrounded by PEEK.

The first end plate 412 may include a first side 411 configured to contact and/or engage a first vertebra and a second side 413 configured to engage the intermediate member 420. While not explicitly shown, the first side 411 may include features configured to engage the bone, such as, but not limited to, teeth, serrations, ridges, projections, bumps, grooves, channels or the like. The second end plate 414 may include a first side 415 configured to engage the intermediate member 420 and a second side 417 configured to contact and/or engage a second vertebra adjacent to the first vertebra. The second side 417 may include features such as, but not limited to teeth, serrations, ridges, projections, bumps, grooves, channels or the like to engage the vertebra.

In some instances, the first and second end plates 412, 414 may be mirror images when assembled with the intermediate member 420. For example, and as discussed in more detail below, the second side 413 of the first end plate 412 may include similar and/or identical features as the first side 415 of the second end plate 414. Similarly, the first side 411 of the first end plate 412 may include similar and/or identical features as the second side 417 of the second end plate 414. In some embodiments, the features of the first and second end plates 412, 414 may be identical, and thus interchangeable. In other embodiments, the first and second end plates 412, 414, may include similar features but in different locations.

In other instances, each endplate 412, 414 may have a different size, shape, curvature and/or angle. For example, a kit of endplates 412, 414 may be provided during a medical procedure of various sizes, shapes, curvatures and/or angles to accommodate anatomical variations and/or lordosis between vertebrae of a spinal column. For instance, the kit may include several pairs of endplates 412, 414 having vertebral body contacting surfaces of varying angles, such as 0°, 1°, 2°, 3°, 4°, 5°, 6°, and/or 7°, or varying radii of curvature. Thus, in view of the modular nature of the implant assembly 400, a surgeon may select any two of the endplates 412, 414 from the kit to provide a customized implant assembly 400 having a desired configuration for a specific anatomy.

The first and second end plates 412, 414 may be spaced a distance from one another by an intermediate member or strut 420 disposed there between. The intermediate member 420 may provide space between the first and second end plates 412, 414 for the insertion of bone growth material. The intermediate member 420 may be sized so as to provide proper spacing between the adjacent vertebrae. In some instances, the intermediate member 420 may be provided as a kit including multiple intermediate members 420 of varying height and/or lengths such that the spacer assembly 400 may be fitted to the patient. In some embodiments, the intermediate member 420 may have a generally horseshoe shape (see FIG. 18) including one or more arms or extensions 422, 424, 426 extending from a connecting member 428 (see FIG. 18) along the posterior side 418 towards the anterior side 416. In some instances, the intermediate member 420 may include a first arm 422 extending along a first lateral side 419 of the assembly 400 and a second arm 424 extending along a second lateral side 421 of the assembly 400. The intermediate member 420 may further include a central arm 426 disposed between the first and second arms 422, 424. Together the arms 422, 424, 426 may define a plurality of cavities 406 for receiving bone growth material. In some embodiments, the intermediate member 420 may further include a first flexing member 423 disposed between the first arm 422 and the central arm 426 and a second flexing member 425 disposed between the second arm 424 and the central arm 426. As will be discussed in more detail with respect to FIGS. 17 and 18 the arms 422, 424, 426 and/or flexing members 423, 425 may include features configured to secure the intermediate member 420 to the end plates 412, 414.

The first and second end plates 412, 414 may further include one or more through holes 408 extending from the first side 411 to the second side 413 of the first end plate 412 and from the first side 415 to the second side 417 of the second end plate 414. For clarity, not all of the through holes 408 have been labeled in the drawings. The through holes 408 may allow bone in-growth from the adjacent vertebrae. In some instances, the through holes 408 may be positioned on the end plates 412, 414 such that they are generally aligned with the cavities 406 defined by the intermediate member 420 and the end plates 412, 414. However, it is contemplated that the through holes 408 may be positioned in any manner desired. It is further contemplated that the through holes 408 may take any desired shape such as, but not limited to, circular, square, rectangular, oval, polygonal, etc. While the interbody spacer assembly 400 is illustrated as having a plurality of through holes 408 within each end plate 412, 414, it is contemplated that the assembly 400 may include any number of through holes 408 desired such as, but not limited to, 1, 2, 4, 4, or more through holes 408. It is further contemplated that in some embodiments one or both end plates 412, 414 may be devoid of through holes 408.

Figure 18:
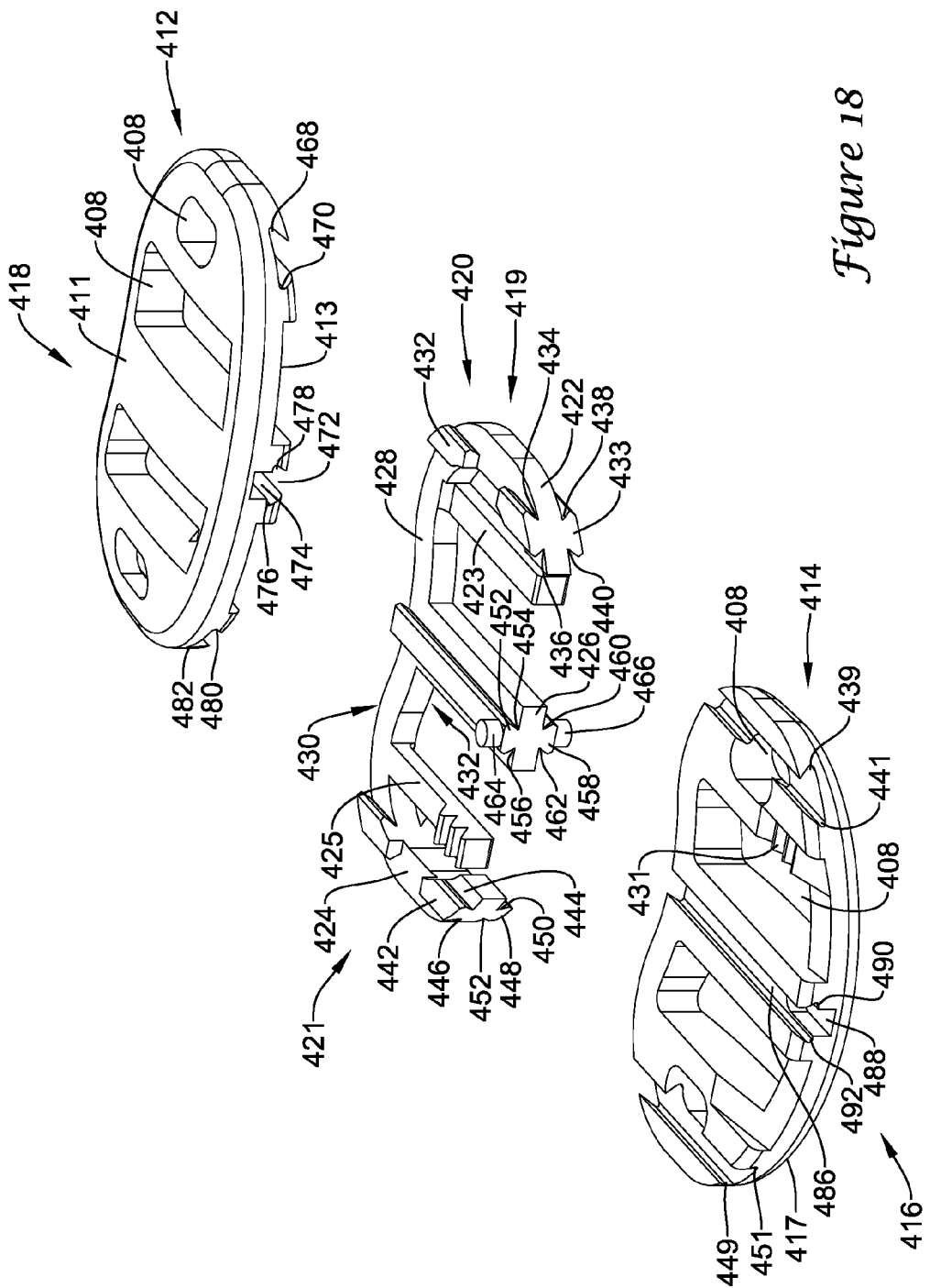
FIG. 18 is an exploded perspective view of the illustrative interbody implant assembly of FIG. 17.

Now referring to FIG. 18, there is shown an exploded perspective view of the illustrative interbody spacer assembly 400 of FIG. 17. The intermediate member 420 may have a generally horseshoe shape formed generally by a first arm 422, a second arm 424 and a connecting member 428. In some instances, the intermediate member 420 may further include a central arm 426, a first flexible member 423, and a second flexible member 425 extending from the connecting member 428. In some instances, the intermediate member 420 may include features configured to prevent over insertion of the intermediate member 420 and/or to prevent the intermediate member 420 from disengaging from the end plates 412, 414.

In some embodiments, the arms 422, 424, 426 may include features configured to engage corresponding features on the end plates 412, 414. For example, the first arm 422 may include a raised portion 432 positioned on a first side 430 of the arm 422. The raised portion 432 (e.g. rail) may include a dovetail groove 434, 436 on either side thereof. The first end plate 412 may include a corresponding pair of dovetail grooves 468, 470 configured to mate with the grooves 434, 436 on the first raised portion 432. It is contemplated that the dovetail grooves 468, 470 on the first end plate 412 may be similar to the dovetail grooves 439, 441 on the second end plate 414 as described below. The first arm 422 may include a second raised portion 433 (e.g. rail) (see FIG. 19) positioned on a second side 432 of the arm 422. The second raised portion 433 may include a dovetail groove 438, 440 on either side thereof. The second end plate 414 may include a corresponding pair of dovetail grooves 439, 441 configured to mate with the grooves 438, 440 on the second raised portion 433. The grooves 439, 441 may be spaced a distance apart from each other generally equal to the distance of the raised portion 433. In some instances, the grooves 439, 441 may face each other to generally define a channel for receiving the raised portion 433 of the first arm 422.

Similarly, the second arm 424 may include a raised portion 442 positioned on a first side 430 of the arm 424. The raised portion 442 may include a dovetail groove 444, 446 on either side thereof. The first end plate 412 may include a corresponding pair of dovetail grooves 480, 482 configured to mate with the grooves 444, 446 on the first raised portion 442. It is contemplated that the dovetail grooves 480, 482 on the first end plate 412 may be similar to the dovetail grooves 451, 449 on the second end plate 414 as described below. While not explicitly shown in FIG. 18, the second arm 424 may include a second raised portion 448 (e.g. rail) (see FIG. 20) positioned on a second side 432 of the arm 424. The second raised portion 448 may include a dovetail groove 450, 452 on either side thereof. The second end plate 414 may include a corresponding pair of dovetail grooves 449, 451 configured to mate with the grooves 450, 452 on the second raised portion 448. The grooves 449, 451 may be spaced a distance apart from each other generally equal to the distance of the raised portion 448. In some instances, the grooves 449, 451 may face each other to generally define a channel for receiving the raised portion 448 of the second arm 424.

When assembled, the mating grooves may align and interlock such that the intermediate member 420 slides between the two end plates 412, 414 and is maintained in a desired orientation. While the grooves have been described as dovetail grooves, it is contemplated the grooves may take any shape desired. It is further contemplated that the grooves may take the shape of some other mating structure. For example, in some instances, the intermediate member 420 may include raised portions configured to engage channels on the end plates 412, 414, or vice versa.

In some embodiments, the central arm 426 may include a first raised portion 452 on a first side 430 of the intermediate member 420. The raised portion 452 may have two dovetail grooves 454, 456 formed on either side thereof. The first end plate 412 may include a groove 472 defined therein. The groove 472 may include a dovetail groove 478, 476 on either side thereof. The dovetail grooves 478, 476 may be configured to mate with the grooves 456, 454 on the first side 430 of the central arm 426. The central arm 426 may further include a second raised portion 458 on a second side 432 of the intermediate member 420. The raised portion 458 may have two dovetail grooves 460, 462 formed on either side thereof (see FIG. 20). The second end plate 414 may include a groove 486 defined therein. The groove 486 may include a dovetail groove 490, 492 on either side thereof. The dovetail grooves 490, 492 may be configured to mate with the grooves 460, 462 on the second side 432 of the central arm 426.

When assembled, the mating grooves may align and interlock such that the intermediate member 420 slides between the two end plates 412, 414 and is maintained in a desired orientation. While the grooves have been described as dovetail grooves, it is contemplated the grooves may take any shape desired. It is further contemplated that the grooves may take the shape of some other mating structure. For example, in some instances, the intermediate member 420 may include raised portions configured to engage channels on the end plates 412, 414, or vice versa.

In some embodiments, the intermediate member 420 may further include features configured to prevent the intermediate member 420 from being advanced too far in the posterior direction. In some embodiments, the central arm 426 may include a first stop member or pin 464 extending from the first side 430 and a second pin 466 extending from the second side 432. The first end plate 412 may include a recessed portion 474 configured to receive the first pin 464. In some instances, the recessed portion 474 may be partially disposed within the central channel 472. For example, the recessed portion 474 may comprise a portion of the channel 472 adjacent to the anterior side 416 and may have a depth greater than a depth of the remainder of the channel 472. Similarly, the second end plate 414 may include a recessed portion 488 configured to receive the second pin 466. In some instances, the recessed portion 488 may be partially disposed within the central channel 486. For example, the recessed portion 488 may comprise a portion of the channel 486 adjacent to the anterior side 416 and may have a depth greater than a depth of the remainder of the channel 486. While described as pins, it is contemplated that the stop members 464, 466 may have any shape or size desired configured to engage the recessed portions 474, 488. Likewise, the recessed portions 474, 488 may take any shape or size suitable to receive the stop members 464, 466. When the intermediate member 420 is assembled within the end plates 412, 414 the stop members 464, 466 may abut the recessed portions 474, 488 such that further movement in the posterior direction is prevented.

In some embodiments, the intermediate member 420 may further include one or more flexing members 423, 425. A first flexing member 423 may be positioned between the first arm 422 and the central arm 426 and may extend from the connecting member 428 towards the anterior side 416. The first flexing member 423 may include a plurality of teeth 427 (see FIG. 20), or other engaging member on the second side 432 thereof configured to engage a plurality of teeth 431 disposed on the second end plate 414. While not explicitly shown, it is contemplated that the first flexing member 423 may additionally include a plurality of teeth on the first side 430. It is further contemplated that the first flexing member 423 may include a plurality of teeth on the first side 430 and not the second side 432. The first flexing member 423 may be configured to flex towards the first end plate 412 during insertion of the intermediate member 420 into the end plates 412, 414. The teeth 427, 431 may be of any size and/or shape desired. For example, the teeth 427, 431 may be serrations, ridges, bumps, grooves, or other mating structure.

A second flexing member 425 may be positioned between the second arm 424 and the central arm 426 and may extend from the connecting member 428 towards the anterior side 416. The second flexing member 425 may include a plurality of teeth 429, or other engaging member on the first side 430 thereof configured to engage a plurality of teeth (not explicitly shown) disposed on the first end plate 412. While not explicitly shown, it is contemplated that the second flexing member 425 may additionally include a plurality of teeth on the second side 432. It is further contemplated that the second flexing member 425 may include a plurality of teeth on the second side 432 and not the first side 430. The second flexing member 425 may be configured to flex towards the second end plate 414 during insertion of the intermediate member 420 into the end plates 412, 414. The teeth 429 may be of any size and/or shape desired. For example, the teeth 429 may be serrations, ridges, bumps, grooves, or other mating structure.

As mentioned above, the first flexing member 423 may be configured to flex towards the first end plate 412 and the second flexing member 425 may be configured to flex towards the second end plate 414. This may allow the flexing members 423, 425, to be slightly deformed in order to allow the intermediate member 420 to be moved in the posterior direction and into engagement with the teeth 431 on the first and second end plates 412, 414. When the flexing members 423, 425 engage the teeth 431 on the first and second end plates 412, 414, the respective teeth may interact such that the intermediate member 420 may not be subsequently moved in the anterior direction. Further, the engagement of the flexing members 423, 425 and the teeth 431 on the first and second end plates 412, 414 may create a stop mechanism such that the intermediate member 420 may not be over-inserted in the posterior direction.

Figure 19:
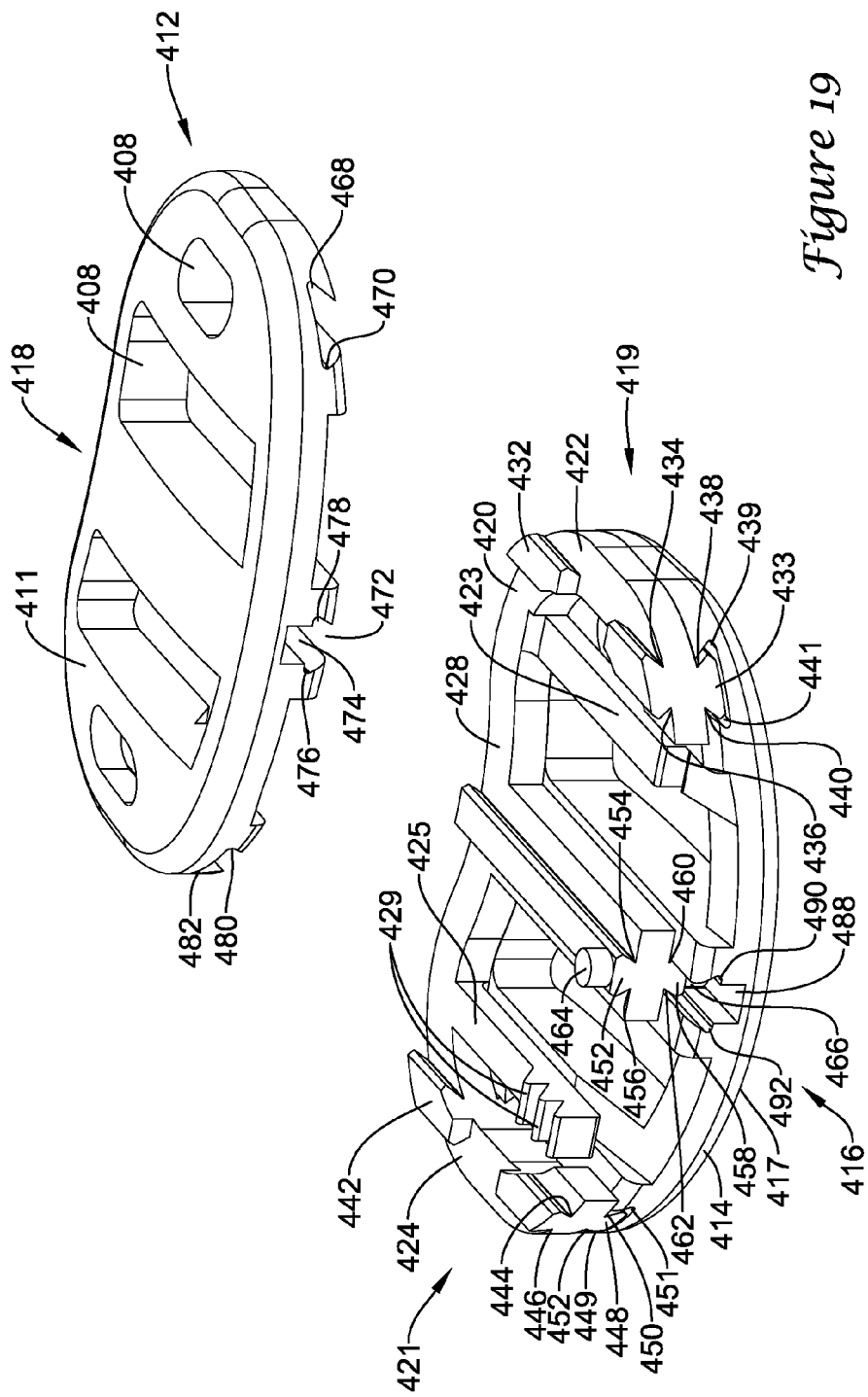
FIG. 19 is an exploded perspective view of the illustrative interbody implant assembly of FIG. 17 partially assembled.

Now referring to FIG. 19, there is shown a partially exploded perspective view of the illustrative interbody spacer assembly 400 of FIG. 17. For illustrative purposes, the intermediate member 420 is shown assembled with the second end plate 414 with the first end plate 412 removed. In some instances, the first and second end plates 412, 414 may be positioned between the vertebral bodies of opposing vertebrae. Once the end plates 412, 414 have been adequately secured, the intermediate member 420 may be slid between the first and second end plates 412, 414 to provide the desired distraction/alignment of the vertebral bodies. For clarity, only the interactions between the second end plate 414 and the intermediate member 420 will be described with respect to FIG. 19. However, it should be understood that the intermediate member 420 and the first end plate 412 may interact in a similar manner as the intermediate member 420 and the second end plate 414.

The intermediate member 420 may be assembled with the second end plate 414 such that the dovetail grooves 438, 440, 450, 452 on the intermediate member 420 engage the dovetail grooves 439, 441, 451, 449 of the second end plate 414. The spacer assembly 400 may be assembled by sliding the intermediate member 420 from the anterior side 416 towards the posterior side 418 while aligning the mating grooves. As the intermediate member 420 is installed, the flexing member 423 may bend slightly towards the first end plate 412 to allow the teeth 427 of the flexing member 423 to engage the teeth 431 on the second end plate 414. The teeth 427, 431 may be structured such that the intermediate number 420 may be moved in the posterior direction but are substantially prevented from being subsequently moved in the anterior direction. It is contemplated the remaining plurality of teeth on the intermediate number 420 are structured in a similar manner and may engage the plurality of teeth on the first and second end plates 412, 414 in a similar manner.

In some embodiments, the intermediate member 420 may be advanced in the posterior direction until the pin 466 on the central arm 426 engages recessed portion 488 of the second end plate 414. When the intermediate member 420 is assembled within the end plates 412, 414 the stop member 466 may abut the recessed portion 488 such that further movement in the posterior direction is prevented.

Figure 20:
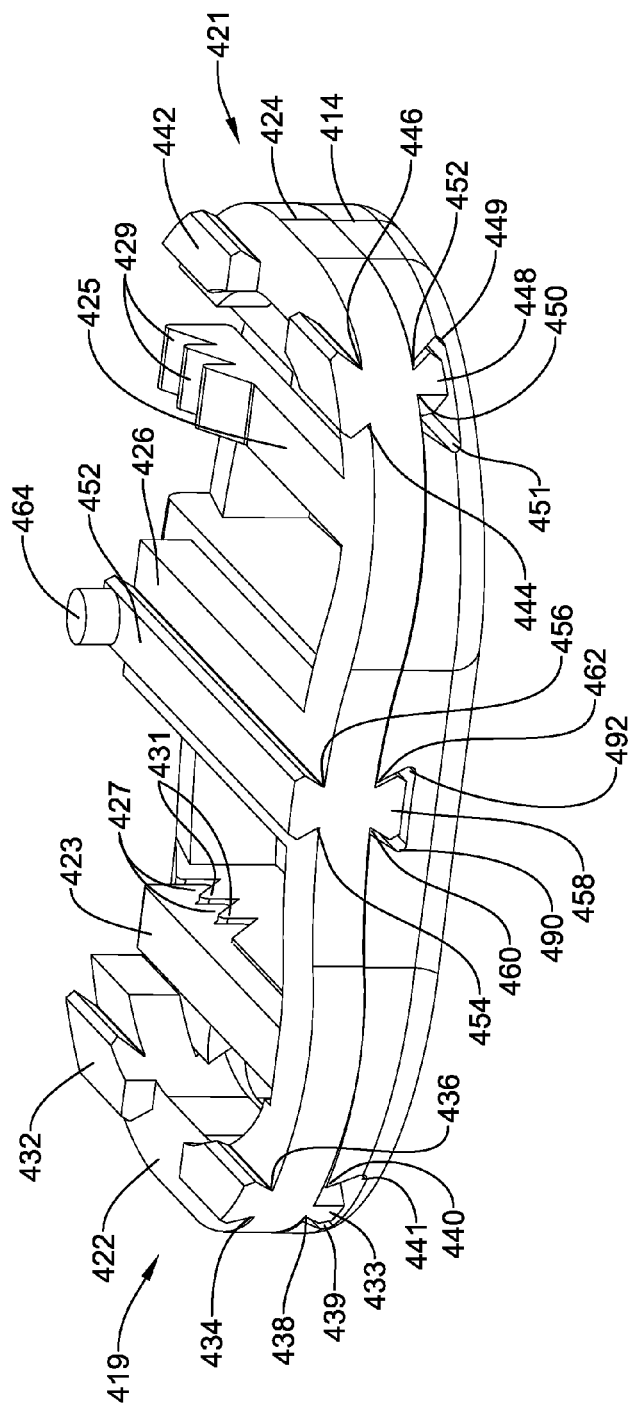
FIG. 20 is a perspective view of the illustrative interbody implant assembly of FIG. 17 partially assembled.

Now referring to FIG. 20, there is shown a partial perspective view of the illustrative interbody spacer assembly 400 of FIG. 17 from the posterior side 418. The first end plate 412 is not illustrated in order to provide a more detailed view of how the intermediate member 420 engages the second end plate 414. As discussed above, the first and second end plates 412, 414 may include similar, features. As such, one of skill in the art will readily appreciate that the features described with respect to the second end plate 414 may be provided on the first end plate and function in a similar manner. In some instances, the teeth 427 of the flexing member 423 may engage the teeth 431 on the second end plate 414.

When assembled, the posterior side 418 of the assembly 400 may be substantially closed such that bone growth material may be contained within the cavities 40 defined by the first end plate 412, the intermediate member 420, and the second end plate 414. The anterior side 416 of the assembly 400 may remain relatively open allowing for the insertion of bone growth material from the anterior side 416.

Figure 21:
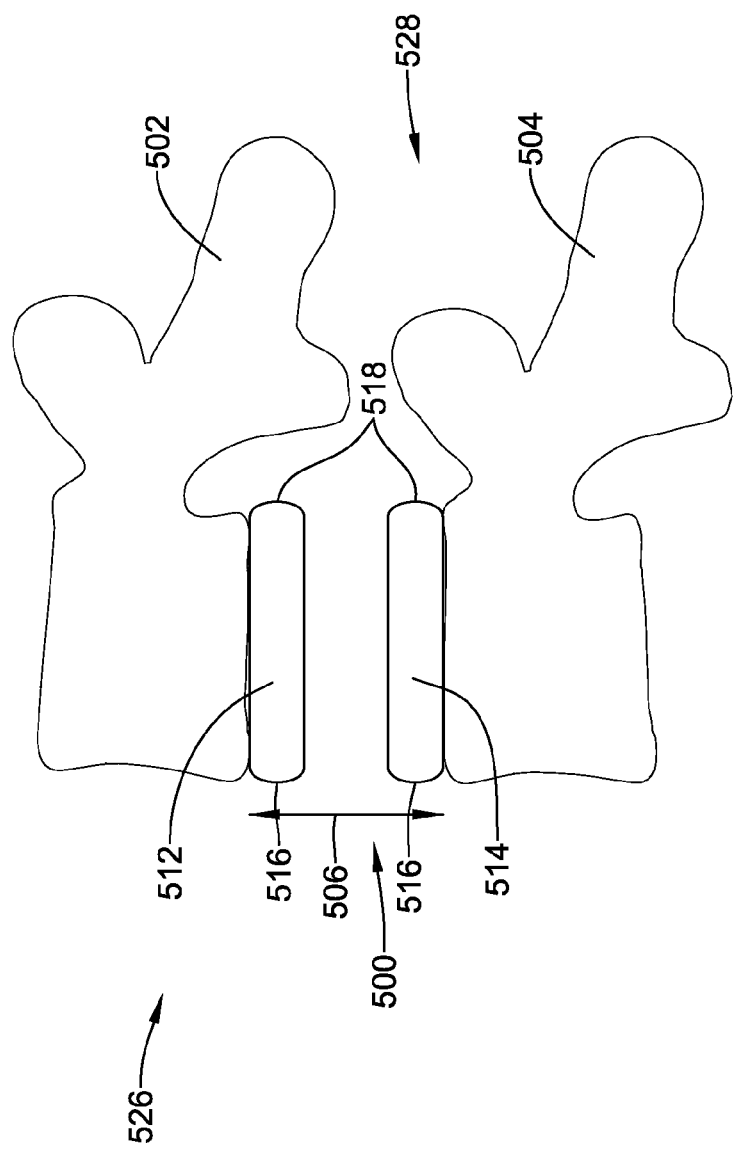
FIGS. 21 and 22 depict an illustrative method of installing an illustrative interbody implant into an intervertebral disc space.
Figure 22:
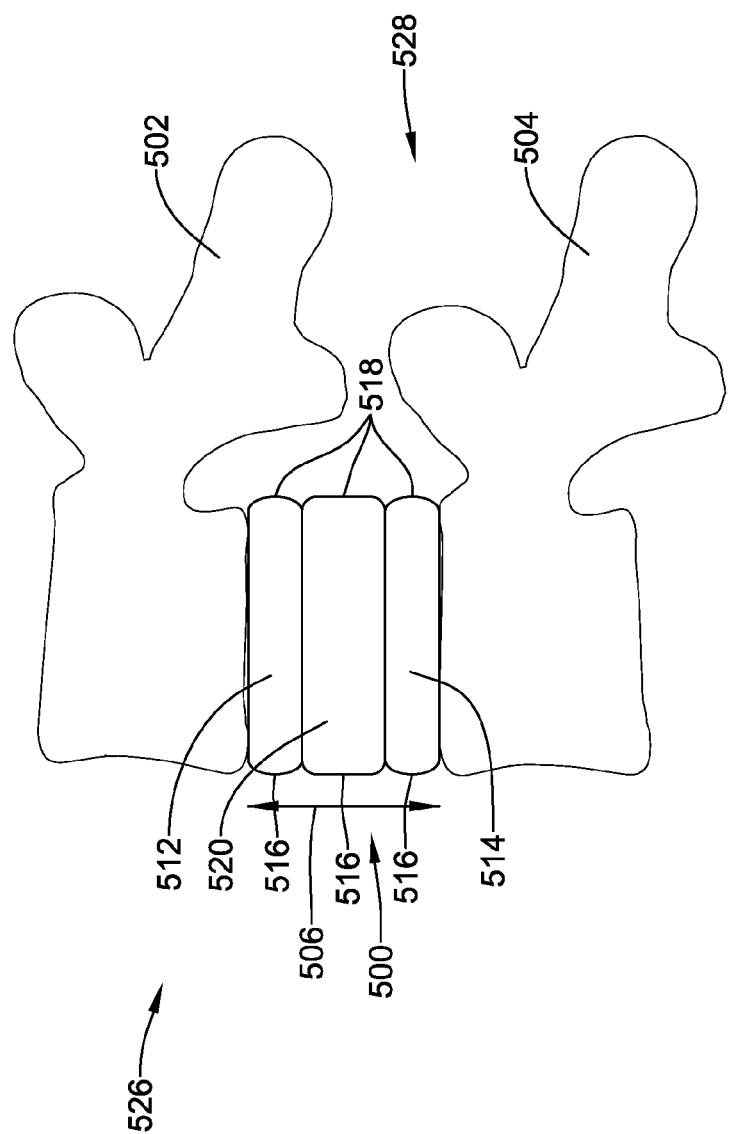

Now referring to FIGS. 21 and 22, there is shown an illustrative method of installing a vertebral implant 500 into an intervertebral disc space. It is contemplated that any of the vertebral implants 10, 100, 200, 300, 400 discussed herein may be installed between two adjacent vertebrae 502, 504 as discussed with respect to FIGS. 21 and 22. In some instances, the diseased or damaged disc material may be removed between two adjacent vertebrae 502, 504 providing a space 506 therebetween. A first end plate 512 may be positioned adjacent to a first vertebra 502 and a second end plate 514 may be positioned adjacent to a second vertebra 504. The assembly 500 may be configured such that when the assembly 500 is inserted between the vertebral bodies of adjacent vertebrae 502, 504, the posterior side 518 is disposed adjacent to the posterior side 528 of the vertebral bodies of the vertebrae and the anterior side 516 is disposed adjacent to the anterior side 526 of the vertebral bodies of the vertebrae. The first and second end plates 512, 514 may include features such as, but not limited to teeth, serrations, ridges, projections, bumps, grooves, channels or the like to engage the vertebra. In some embodiments, the first and second end plates 512, 514 may include features configured to receive a screw of other mechanism configured to secure the end plates 512, 514 to a vertebra at an oblique angle.

Once the end plates 512, 514 have been positioned, an intermediate member 520 may be slid between the first and second end plates 512, 514 providing a desired distraction and/or alignment of the vertebrae. In some embodiments, the intermediate member 520 may be assembled between the first and second end plates 512, 514 from the anterior side 526 of the vertebrae. For example, the intermediate member 520 may be slid in the posterior direction until the intermediate member 520 fully engages the end plates 512, 514. In some instances, the intermediate member 520 and the end plates 512, 514 may include mating features configured to align the intermediate member 520 with the end plates 512, 514 and/or to secure the intermediate member 520 between the end plates 512, 514. The intermediate member 520 and the end plates 512, 514 may also include features to prevent the intermediate member 520 from being inserted too far in the posterior direction. In some instances, once the intermediate member 520 has been positioned between the end plates 512, 514 bone growth material may be inserted into a cavity defined by the end plates 512, 514 and the intermediate member 520.

It is contemplated that the space 506 between adjacent vertebrae may vary from patient to patient. In order to provide an implant 500 capable of providing the desired amount of distraction between adjacent vertebrae 502, 504, the implant 500 may be provided as a kit. The kit may include multiple intermediate members 520 of varying heights and/or lengths such that a physician may select an intermediate member 520 to provide the desired amount of distraction.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An interbody vertebral implant having a posterior side and an anterior side, the implant comprising:
    a first end plate having a first side configured to engage a first vertebra and a second side;
    a second end plate having a first side and a second side configured to engage a second vertebra; and
    an intermediate member having a first side and a second side and including a first arm extending along a first lateral side, a second arm extending along a second lateral side, and a central arm disposed between the first arm and the second arm, the intermediate member slidably disposed between the first and second end plates;
    wherein the first arm, the second arm, and the central arm are connected along the posterior side by a connecting member;
    wherein the first end plate comprises a central channel extending along the second side of the first end plate from the anterior side toward the posterior side and the second end plate comprises a central channel extending along the first side of the second end plate from the anterior side toward the posterior side; and
    wherein a pair of dovetail grooves extend along at least a portion of the central channels of the first and second end plates.

2. The interbody vertebral implant of claim 1, further comprising a cavity configured to receive bone growth material to facilitate fusion between the first vertebra and the second vertebra.

3. The interbody vertebral implant of claim 1, wherein the central channels of the first and second end plates comprise an enlarged region adjacent the anterior side.

4. The interbody vertebral implant of claim 3, wherein the central arm comprises a "Y" shaped fork adjacent the anterior side.

5. The interbody vertebral implant of claim 4, wherein the central arm comprises a first pair of dovetail grooves on the first side and a second pair of dovetail grooves on the second side.

6. The interbody vertebral implant of claim 4, wherein the fork is configured to engage the enlarged regions of the central channels of the first and second end plates.

7. The interbody vertebral implant of claim 5, wherein the first pair of dovetail grooves on the central arm are configured to engage the pair of dovetail grooves on the first end plate and the second pair of dovetail grooves on the central arm are configured to engage the pair of dovetail grooves on the second end plate.

8. The interbody vertebral implant of claim 1, wherein the first arm includes a first stop member on the first side thereof and a second stop member on the second side thereof and the second arm includes a third stop member on the first side thereof and a fourth stop member on the second side thereof.

9. The interbody vertebral implant of claim 8, wherein the first end plate includes a first recessed portion adjacent the anterior side and the first lateral side and a second recessed portion adjacent the anterior side and the second lateral side and wherein the second end plate includes a third recessed portion adjacent the anterior side and the first lateral side and a fourth recessed portion adjacent the anterior side and the second lateral side.

10. The interbody vertebral implant of claim 9, wherein the first stop member is configured to engage the first recessed portion, the second stop member is configured to engage the third recessed portion, the third stop member is configured to engage the second recessed portion, and the fourth stop member is configured to engage the fourth recessed portion.

11. An interbody vertebral implant having a posterior side and an anterior side, the implant comprising:
    a first end plate having a first side configured to engage a first vertebra and a second side;
    a second end plate having a first side and a second side configured to engage a second vertebra; and
    an intermediate member having a first side, a second side, a first lateral side, and a second lateral side, the first side of the intermediate member configured to engage the second side of the first end plate and the second side of the intermediate member configured to engage the first side of the second end plate;
    wherein the intermediate member comprises a connecting member, a first arm extending from the connecting member towards the anterior side along the first lateral side, a second arm extending from the connecting member towards the anterior side along the second lateral side, and a central arm extending from the connecting member towards the anterior side between the first and second arms; and
    wherein the central arm includes a fork having a first prong and a second prong adjacent to the anterior side.

12. The interbody vertebral implant of claim 11, further comprising:
    a first central channel extending along the second side of the first end plate from the anterior side toward the posterior side and including an enlarged region adjacent to the anterior side;
    a second central channel extending along the first side of the first end plate from the anterior side toward the posterior side and including an enlarged region adjacent to the anterior side;
    wherein the first and second central channels are configured to receive the central arm such that the fork is disposed with the enlarged regions of the channels.

13. The interbody vertebral implant of claim 11, further comprising a first pair of dovetail grooves along the first side of the first arm, a second pair of dovetail grooves along the second side of the first arm, a third pair of dovetail grooves along the first side of the second arm, and a fourth pair of dovetail grooves along the second side of the second arm.

14. The interbody vertebral implant of claim 13, further comprising a fifth pair of dovetail grooves adjacent the first lateral side on the second side of the first end plate, a sixth pair of dovetail grooves adjacent the second lateral side on the second side of the first end plate, a seventh pair of dovetail grooves adjacent the first lateral side on the first side of the second end plate, and an eighth pair of dovetail grooves adjacent the second lateral side on the first side of the second end plate.

15. The interbody vertebral implant of claim 14, wherein the first pair of dovetail grooves are configured to engage the fifth pair of dovetail grooves, the second pair of dovetail grooves are configured to engage the seventh pair of dovetail grooves, the third pair of dovetail grooves are configured to engage the sixth pair of dovetail grooves, and the fourth pair of dovetail grooves are configured to engage the eighth pair of dovetail grooves.

16. The interbody vertebral implant of claim 11, further comprising at least one stop member on at least one of the first or second arms adjacent to the anterior side.

17. The interbody vertebral implant of claim 16, further comprising at least one recessed portion formed in at least one of the first or second end plates configured to receive the at least one stop member.

18. An interbody vertebral implant having a posterior side and an anterior side, the implant comprising:
a first end plate having a first side configured to engage a first vertebra and a second side;
a second end plate having a first side and a second side configured to engage a second vertebra; and
an intermediate member having a first side configured to engage the second side of the first end plate and a second side configured to engage the first side of the second end plate;
wherein the intermediate member comprises:
a connecting member extending from a first lateral side to a second lateral side along the posterior side;
a first arm extending from the connecting member towards the anterior side along the first lateral side and including at least one stop member adjacent the anterior side;
a second arm extending from the connecting member towards the anterior side along the second lateral side and including at least one stop member; and
a central arm extending from the connecting member towards the anterior side between the first and second arms and including a fork having a first prong and a second prong adjacent to the anterior side;
wherein the second side of the first end plate comprises means for engaging the first side of the intermediate member and the first side of the second end plate comprises means for engaging the second side of the intermediate member.

19. An interbody vertebral implant having a posterior side and an anterior side, the implant comprising:
a first end plate having a first side configured to engage a first vertebra and a second side;
a second end plate having a first side and a second side configured to engage a second vertebra;
an intermediate member having a first side and a second side and including a first arm extending along a first lateral side and a second arm extending along a second lateral side, the intermediate member slidably disposed between the first and second end plates, the first arm of the intermediate member including a first hole configured for receiving a first vertebral anchor therethrough to secure the implant to the first vertebra, and the second arm of the intermediate member including a second hole configured for receiving a second vertebral anchor therethrough to secure the implant to the second vertebra; and
a first locking mechanism configured to prevent movement of the intermediate member relative to the first end plate while simultaneously preventing the first vertebral anchor from backing out of the first hole.

20. The interbody vertebral implant of claim 19, further comprising a second locking mechanism configured to prevent movement of the intermediate member relative to the second end plate while simultaneously preventing the second vertebral anchor from backing out of the second hole.

21. The interbody vertebral implant of claim 20, wherein rotation of the first locking mechanism causes a first portion of the first locking mechanism to cover the first hole and a second portion of the first locking mechanism to be disposed in a groove of the first end plate; and
wherein rotation of the second locking mechanism causes a first portion of the second locking mechanism to cover the second hole and a second portion of the second locking mechanism to be disposed in a groove of the second end plate.

22. The interbody vertebral implant of claim 19, wherein rotation of the first locking mechanism causes a first portion of the first locking mechanism to cover the first hole and a second portion of the first locking mechanism to be disposed in a groove of the first end plate.

23. An interbody vertebral implant having a posterior side and an anterior side, the implant comprising:
a first end plate having a first side configured to engage a first vertebra and a second side;
a second end plate having a first side and a second side configured to engage a second vertebra; and
an intermediate member having a first side and a second side and including a first arm extending along a first lateral side, a second arm extending along a second lateral side, and a central arm disposed between the first arm and the second arm, the intermediate member slidably disposed between the first and second end plates;
wherein the first arm, the second arm, and the central arm are connected along the posterior side by a connecting member; and
wherein the first arm includes a first stop member on the first side thereof and a second stop member on the second side thereof and the second arm includes a third stop member on the first side thereof and a fourth stop member on the second side thereof.

24. The interbody vertebral implant of claim 23, wherein the first end plate includes a first recessed portion adjacent the anterior side and the first lateral side and a second recessed portion adjacent the anterior side and the second lateral side and wherein the second end plate includes a third recessed portion adjacent the anterior side and the first lateral side and a fourth recessed portion adjacent the anterior side and the second lateral side.

25. The interbody vertebral implant of claim 24, wherein the first stop member is configured to engage the first recessed portion, the second stop member is configured to engage the third recessed portion, the third stop member is configured to engage the second recessed portion, and the fourth stop member is configured to engage the fourth recessed portion.

* * * * *